United States Patent
Maron et al.

(10) Patent No.: US 9,605,047 B2
(45) Date of Patent: Mar. 28, 2017

(54) COMPOSITIONS AND METHODS FOR TREATING HYPERTENSION

(71) Applicant: The Brigham and Women's Hospital, Inc., Boston, MA (US)

(72) Inventors: Bradley Maron, Sharon, MA (US); Joseph Loscalzo, Dover, MA (US); Jane Leopold, Chestnut Hill, MA (US)

(73) Assignee: The Brigham and Womens's Hospital, Inc., Boston, MA (US)

( * ) Notice: Subject to any disclaimer, the term of this patent is extended or adjusted under 35 U.S.C. 154(b) by 35 days.

(21) Appl. No.: 14/390,408

(22) PCT Filed: Apr. 3, 2013

(86) PCT No.: PCT/US2013/035075
§ 371 (c)(1),
(2) Date: Oct. 3, 2014

(87) PCT Pub. No.: WO2013/152076
PCT Pub. Date: Oct. 10, 2013

(65) Prior Publication Data
US 2015/0203563 A1    Jul. 23, 2015

Related U.S. Application Data

(60) Provisional application No. 61/620,187, filed on Apr. 4, 2012.

(51) Int. Cl.
| | | |
|---|---|---|
| C07K 14/705 | (2006.01) | |
| G01N 33/50 | (2006.01) | |
| A61K 38/17 | (2006.01) | |
| A61K 38/00 | (2006.01) | |

(52) U.S. Cl.
CPC ......... C07K 14/705 (2013.01); G01N 33/502 (2013.01); *A61K 38/00* (2013.01); *A61K 38/177* (2013.01); *G01N 2333/726* (2013.01); *G01N 2440/20* (2013.01); *G01N 2500/04* (2013.01); *G01N 2500/10* (2013.01)

(58) Field of Classification Search
CPC ............................ C07K 14/705; A61K 38/177
USPC ......................................................... 530/350
See application file for complete search history.

(56) References Cited

U.S. PATENT DOCUMENTS

| | | | |
|---|---|---|---|
| 5,883,075 A | 3/1999 | Wakimasu et al. | |
| 2004/0258674 A1* | 12/2004 | Jalili | A23L 1/296 424/94.1 |
| 2006/0166894 A1* | 7/2006 | Haj-Yehia | A61K 31/16 514/149 |
| 2009/0234011 A1* | 9/2009 | Goldstein | A61K 31/16 514/563 |
| 2011/0129523 A1* | 6/2011 | Guilford | A61K 9/127 424/450 |

FOREIGN PATENT DOCUMENTS

| | | |
|---|---|---|
| WO | 2005/095972 | 10/2005 |

OTHER PUBLICATIONS

Beswick R A (Hypertension 37:781-786, 2001).*
Kokubu et al., Jpn Circ J., 46(10):1095-7, (982), Is captopril effective in primary pulmonary hypertension?
Bansal et al., Contemp Clin Trials.,30(5):392-9, (2009), "Role of vasopressin and aldosterone in pulmonary arterial hypertension: A pilot study."
Michelakis, Heart Fail Rev., 8(1):5-21., (2003), "The role of the NO axis and its therapeutic implications in pulmonary arterial hypertension."
Maron, et al, J. Biol. Chem., 2009, vol. 284, No. 12, pp. 7665-7672.
Okamoto et al, J. Biol. Chem., 1997, vol. 272, No. 34, pp. 21589-21596.

* cited by examiner

*Primary Examiner* — David Lukton
(74) *Attorney, Agent, or Firm* — Nixon Peabody LLP

(57) ABSTRACT

The technology described herein is directed to agents that reduce the level of oxidant-modified ET-B Cys405, Cys403, or Cys402 and the identification and use of such agents for, e.g. to treat hypertension.

8 Claims, 15 Drawing Sheets

4A

| | V | MCT | MCT+Sp |
|---|---|---|---|
| HR (beats/min) | 255 ± 12 | 261 ± 8 | 259 ± 14 |
| MAP (mmHg) | 67.1 ± 2.9 | 62.5 ± 2.2 | 60.7 ± 5.4 |
| CI (ml/min/g) | 138.3 ± 39.3 | 86.9 ± 8.5 | 94.3 ± 15.3 |
| LVEDP (mmHg) | 3.2 ± 0.6 | 1.8 ± 0.5 | 2.8 ± 0.9 |
| PASP (mmHg) | 26.1 ± 2.2 | 60.3 ± 5.2 | 39.5 ± 4.1* |
| PVRi (mmHg*min*g/ml) | 10.4 ± 3.0 | 35.9 ± 3.2** | 21.5 ± 3.2* |
| SVRi (mmHg*min*g/ml) | 73.8 ± 7.2 | 68.4 ± 6.0 | 66.4 ± 10.7 |

4B

6A 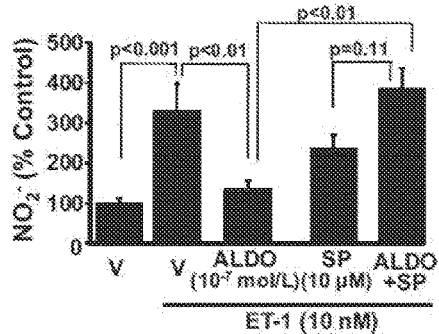
6B 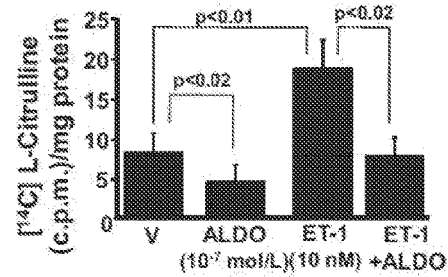
6C 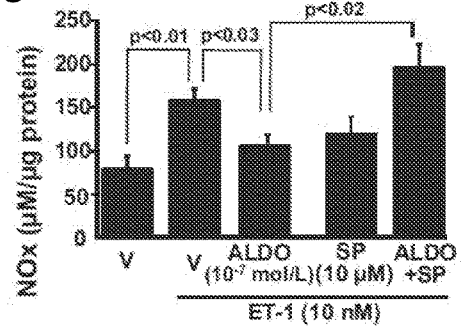
6D 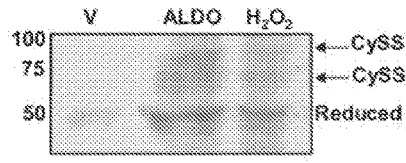
6E 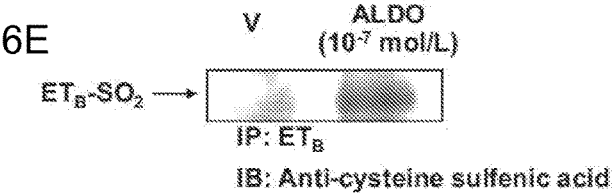
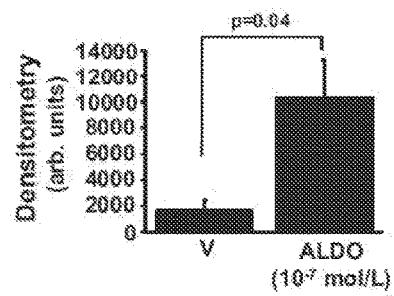
Figures 6A-6E

10A

10B

| Condition | RV/LV+Septum Weight |
|---|---|
| Vehicle | 0.22 ± 0.05 |
| SP | 0.26 ± 0.02 |
| MCT | 0.43 ± 0.07* |
| MCT+SP | 0.35 ± 0.04 |

13A
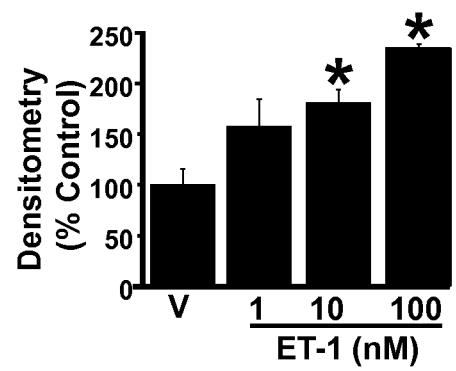
13B
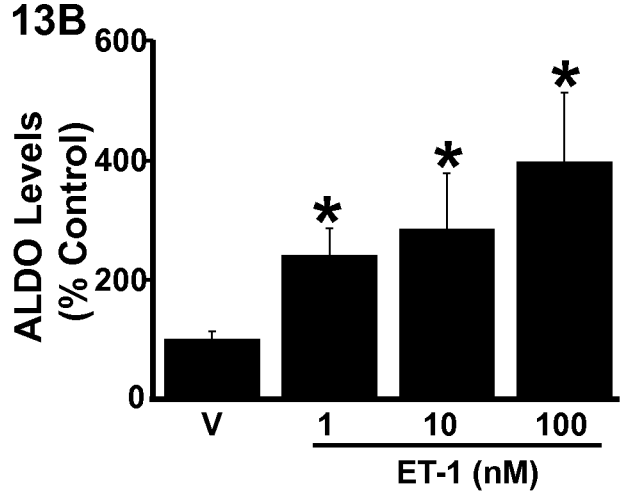
Figures 13A-13B

15A

15B

15C

SEQUENCE LISTING

<160> NUMBER OF SEQ ID NOS: 7

<210> SEQ ID NO 1
<211> LENGTH: 43
<212> TYPE: PRT
<213> ORGANISM: Homo sapiens

<400> SEQUENCE: 1

Cys Leu Cys Cys Trp Cys Gln Ser Phe Glu Glu Lys Gln Ser Leu Glu
1               5                   10                  15

Glu Lys Gln Ser Cys Leu Lys Phe Lys Ala Asn Asp His Gly Tyr Asp
            20                  25                  30

Asn Phe Arg Ser Ser Asn Lys Tyr Ser Ser Ser
        35                  40

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
gagaaaggag aggccaggtc                                          20

```
<210> SEQ ID NO 3
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
caggaacctg ctctggaaac                                                  20

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gagaaaggag aggccaggtc                                                  20

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
caggaacctg ctctggaaac                                                  20

<210> SEQ ID NO 6
<211> LENGTH: 4296
<212> TYPE: DNA
<213> ORGANISM: Homo sapiens

<400> SEQUENCE: 6
acattccggt gggggactct ggccagcccg agcaacgtgg atcctgagag cactcccagg        60
taggcatttg ccccggtggg acgccttgcc agagcagtgt gtggcaggcc cccgtggagg       120
atcaacacag tggctgaaca ctgggaagga actggtactt ggagtctgga catctgaaac       180
ttggctctga aactgcggag cggccaccgg acgccttctg gagcaggtag cagcatgcag       240
ccgcctccaa gtctgtgcgg acgcgccctg gttgcgctgg ttcttgcctg cggcctgtcg       300
cggatctggg gagaggagag aggcttcccg cctgacaggg ccactccgct tttgcaaacc       360
gcagagataa tgacgccacc cactaagacc ttatggccca agggttccaa cgccagtctg       420
gcgcggtcgt tggcacctgc ggaggtgcct aaaggagaca ggacggcagg atctccgcca       480
cgcaccatct cccctccccc gtgccaagga cccatcgaga tcaaggagac tttcaaatac       540
atcaacacgg ttgtgtcctg ccttgtgttc gtgctgggga tcatcgggaa ctccacactt       600
ctgagaatta tctacaagaa caagtgcatg cgaaacggtc ccaatatctt gatcgccagc       660
ttggctctgg agacctgct gcacatcgtc attgacatcc ctatcaatgt ctacaagctg       720
ctggcagagg actggccatt tggagctgag atgtgtaagc tggtgcctt catacagaaa       780 gcctccgtgg gaatcactgt gctgagtcta tgtgctctga gtattgacag atatcgagct       840
gttgcttctt ggagtagaat taaaggaatt ggggttccaa aatggacagc agtagaaatt       900
gttttgattt gggtggtctc tgtggttctg gctgtccctg aagccatagg ttttgatata       960
attacgatgg actacaaagg aagttatctg cgaatctgct tgcttcatcc cgttcagaag      1020
```

```
acagctttca tgcagttttta caagacagca aaagattggt ggctattcag tttctatttc    1080
tgcttgccat tggccatcac tgcattttt tatacactaa tgacctgtga aatgttgaga     1140
aagaaaagtg gcatgcagat tgctttaaat gatcacctaa agcagagacg ggaagtggcc    1200
aaaaccgtct tttgcctggt ccttgtcttt gccctctgct ggcttcccct tcacctcagc    1260
aggattctga agctcactct ttataatcag aatgatccca atagatgtga acttttgagc    1320
tttctgttgg tattggacta tattggtatc aacatggctt cactgaattc ctgcattaac    1380
ccaattgctc tgtatttggt gagcaaaaga ttcaaaaact gctttaagtc atgcttatgc    1440
tgctggtgcc agtcatttga agaaaaacag tccttggagg aaaagcagtc gtgcttaaag    1500
ttcaaagcta atgatcacgg atatgacaac ttccgttcca gtaataaata cagctcatct    1560
tgaaagaaga actattcact gtatttcatt ttctttatat tggaccgaag tcattaaaac    1620
aaaatgaaac atttgccaaa acaaaacaaa aactatgta tttgcacagc acactattaa     1680
aatattaagt gtaattattt taacactcac agctacatat gacattttat gagctgttta    1740
cggcatggaa agaaaatcag tgggaattaa gaaagcctcg tcgtgaaagc acttaatttt    1800
ttacagttag cacttcaaca tagctcttaa caacttccag gatattcaca caacacttag    1860
gcttaaaaat gagctcactc agaatttcta ttctttctaa aaagagattt attttaaat     1920 caatgggact ctgatataaa ggaagaataa gtcactgtaa aacagaactt ttaaatgaag    1980
cttaaattac tcaatttaaa attttaaaat cctttaaaac aacttttcaa ttaatattat    2040
cacactatta tcagattgta attagatgca aatgagagag cagtttagtt gttgcatttt    2100
tcggacactg gaaacattta aatgatcagg agggagtaac agaaagagca aggctgtttt    2160
tgaaaatcat tacactttca ctagaagccc aaacctcagc attctgcaat atgtaaccaa    2220
catgtcacaa acaagcagca tgtaacagac tggcacatgt gccagctgaa tttaaaatat    2280
aatactttta aaagaaaat tattacatcc tttacattca gttaagatca aacctcacaa     2340
agagaaatag aatgtttgaa aggctatccc aaaagacttt tttgaatctg tcattcacat    2400
accctgtgaa gacaatacta tctacaattt tttcaggatt attaaaatct tcttctttca    2460
ctatcgtagc ttaaactctg tttggttttg tcatctgtaa atacttacct acatacactg    2520
catgtagatg attaaatgag ggcaggccct gtgctcatag ctttacgatg gagagatgcc    2580
agtgacctca taataaagac tgtgaactgc ctggtgcagt gtccacatga caagggggca    2640
ggtagcaccc tctctcaccc atgctgtggt taaaatggtt tctagcatat gtataatgct    2700
atagttaaaa tactatttt caaaatcata cagattagta catttaacag ctacctgtaa     2760
agcttattac taattttttgt attattttg taaatagcca atagaaaagt ttgcttgaca    2820
tggtgctttt ctttcatcta gaggcaaaac tgctttttga gaccgtaaga acctcttagc    2880
tttgtgcgtt cctgcctaat ttttatatct tctaagcaaa gtgccttagg atagcttggg    2940
atgagatgtg tgtgaaagta tgtacaagag aaaacgaaag agagaggaaa tgaggtgggg    3000
ttggaggaaa cccatgggga cagattccca ttcttagcct aacgttcgtc attgcctcgt    3060
cacatcaatg caaaaggtcc tgattttgtt ccagcaaaac acagtgcaat gttctcagag    3120
tgactttcga aataaattgg gcccaagagc tttaactcgg tcttaaaata tgcccaaatt    3180
tttactttgt ttttctttta ataggctggg ccacatgttg gaaataagct agtaatgttg    3240
ttttctgtca atattgaatg tgatggtaca gtaaaccaaa acccaacaat gtggccagaa    3300
agaaagagca ataataatta attcacacac catatggatt ctatttataa atcacccaca    3360
```

```
aacttgttct ttaatttcat cccaatcact ttttcagagg cctgttatca tagaagtcat    3420
tttagactct caattttaaa ttaattttga atcactaata ttttcacagt ttattaatat    3480
atttaatttc tatttaaatt ttagattatt tttattacca tgtactgaat ttttacatcc    3540
tgataccctt tccttctcca tgtcagtatc atgttctcta attatcttgc caaattttga    3600
aactacacac aaaaagcata cttgcattat ttataataaa attgcattca gtggcttttt    3660
aaaaaaatgt ttgattcaaa actttaacat actgataagt aagaaacaat tataatttct    3720
ttacatactc aaaaccaaga tagaaaaagg tgctatcgtt caacttcaaa acatgtttcc    3780
tagtattaag gactttaata tagcaacaga caaaattatt gttaacatgg atgttacagc    3840
tcaaaagatt tataaaagat tttaacctat tttctccctt attatccact gctaatgtgg    3900
atgtatgttc aaacaccttt tagtattgat agcttacata tggccaaagg aatacagttt    3960
atagcaaaac atgggtatgc tgtagctaac tttataaaag tgtaatataa caatgtaaaa    4020
aattatatat ctgggaggat ttttggttg cctaaagtgg ctatagttac tgatttttta     4080
ttatgtaagc aaaaccaata aaatttaag ttttttttaac aactaccta ttttttcactg    4140 tacagacact aattcattaa atactaattg attgtttaaa agaaatataa atgtgacaag    4200
tggacattat ttatgttaaa tatacaatta tcaagcaagt atgaagttat tcaattaaaa    4260
tgccacattt ctggtctctg ggaaaaaaaa aaaaaa                              4296
```

<210> SEQ ID NO 7
<211> LENGTH: 442
<212> TYPE: PRT
<213> ORGANISM: Homo sapiens

<400> SEQUENCE: 7

```
Met Gln Pro Pro Ser Leu Cys Gly Arg Ala Leu Val Ala Leu Val
1               5                   10                  15

Leu Ala Cys Gly Leu Ser Arg Ile Trp Gly Glu Glu Arg Gly Phe Pro
            20                  25                  30

Pro Asp Arg Ala Thr Pro Leu Leu Gln Thr Ala Glu Ile Met Thr Pro
        35                  40                  45

Pro Thr Lys Thr Leu Trp Pro Lys Gly Ser Asn Ala Ser Leu Ala Arg
    50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
            100                 105                 110

Val Leu Gly Ile Ile Gly Asn Ser Thr Leu Leu Arg Ile Ile Tyr Lys
        115                 120                 125

Asn Lys Cys Met Arg Asn Gly Pro Asn Ile Leu Ile Ala Ser Leu Ala
    130                 135                 140

Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
            180                 185                 190

Cys Ala Leu Ser Ile Asp Arg Tyr Arg Ala Val Ala Ser Trp Ser Arg
        195                 200                 205
```

-continued

```
Ile Lys Gly Ile Gly Val Pro Lys Trp Thr Ala Val Glu Ile Val Leu
    210             215                 220
Ile Trp Val Val Ser Val Val Leu Ala Val Pro Glu Ala Ile Gly Phe
225             230                 235                 240
Asp Ile Ile Thr Met Asp Tyr Lys Gly Ser Tyr Leu Arg Ile Cys Leu
            245                 250                 255
Leu His Pro Val Gln Lys Thr Ala Phe Met Gln Phe Tyr Lys Thr Ala
            260                 265                 270
Lys Asp Trp Trp Leu Phe Ser Phe Tyr Phe Cys Leu Pro Leu Ala Ile
            275                 280                 285
Thr Ala Phe Phe Tyr Thr Leu Met Thr Cys Glu Met Leu Arg Lys Lys
290                 295                 300
Ser Gly Met Gln Ile Ala Leu Asn Asp His Leu Lys Gln Arg Arg Glu
305                 310                 315                 320
Val Ala Lys Thr Val Phe Cys Leu Val Leu Val Phe Ala Leu Cys Trp
            325                 330                 335
Leu Pro Leu His Leu Ser Arg Ile Leu Lys Leu Thr Leu Tyr Asn Gln
            340                 345                 350
Asn Asp Pro Asn Arg Cys Glu Leu Leu Ser Phe Leu Leu Val Leu Asp
            355                 360                 365
Tyr Ile Gly Ile Asn Met Ala Ser Leu Asn Ser Cys Ile Asn Pro Ile
    370                 375                 380
Ala Leu Tyr Leu Val Ser Lys Arg Phe Lys Asn Cys Phe Lys Ser Cys
385                 390                 395                 400
Leu Cys Cys Trp Cys Gln Ser Phe Glu Glu Lys Gln Ser Leu Glu Glu
            405                 410                 415
Lys Gln Ser Cys Leu Lys Phe Lys Ala Asn Asp His Gly Tyr Asp Asn
            420                 425                 430
Phe Arg Ser Ser Asn Lys Tyr Ser Ser Ser
        435                 440
```

COMPOSITIONS AND METHODS FOR TREATING HYPERTENSION

CROSS-REFERENCE TO RELATED APPLICATIONS

This application is a 35 U.S.C. §371 National Phase Entry Application of International Application No. PCT/US13/35075 filed Apr. 3, 2013, and which claims benefit under 35 U.S.C. §119(e) of U.S. Provisional Application No. 61/620,187 filed Apr. 4, 2012, the contents of which are incorporated herein by reference in their entireties.

GOVERNMENT SUPPORT

This invention was made with federal funding under Grant Nos. HL105301, HL61795, HL48743, HL107192, HL070819, and HL108630 awarded by the National Institutes of Health. The U.S. government has certain rights in the invention.

SEQUENCE LISTING

The instant application contains a Sequence Listing which has been submitted in ASCII format via EFS-Web and is hereby incorporated by reference in its entirety. Said ASCII copy, created on Apr. 2, 2013, is named 043214-077430-PCT_SL.txt and is 11,109 bytes in size.

TECHNICAL FIELD

The technology described herein relates to the production of endothelial nitric oxide via regulation of ET-B via oxidative modification of certain residues and e.g. the treatment of hypertension.

BACKGROUND

Pulmonary arterial hypertension (PAH), is a type of hypertension (i.e. high blood pressure) which has a 2-3 year median survival time if left untreated, typically leading to heart failure. Mortality is particularly high in pregnant women. Many treatments for PAH seek to increase the level of pulmonary vascular nitric oxide, which causes vasodilation, thereby lowering blood pressure. However, these treatments lack long-term efficacy, providing only temporary relief (Michelakis E D. Heart Fail Rev. 2003;8(1):5-21).

SUMMARY

As described herein, the inventors have discovered that production of endothelial nitric oxide is regulated, at least in part, by oxidative modifications of certain residues of ET-B. Accordingly, provided herein are methods of increasing nitric oxide production, increasing vasodilatory signaling, and/or treating, e.g. hypertension by administering agents that reduce the level of the oxidative modifications of ET-B.

In one aspect, described herein is a method of treating hypertension in a subject in need thereof, the method comprising administering an agent that reduces the level of oxidant-modified ET-B Cys405, Cys403, or Cys402. In some embodiments, the subject is in need of treatment for a condition selected from the group consisting of systemic hypertension and pulmonary arterial hypertension. In one aspect, described herein is a method of potentiating or increasing nitric oxide vasodilatory signaling activity, the method comprising administering an agent that reduces the level of oxidant-modified ET-B Cys405, Cys403, or Cys402. In some embodiments, the agent is an ET-B polypeptide comprising an oxidant-resistant mutation at Cys405, Cys403, or Cys402. In some embodiments, the agent is a nucleic acid encoding an ET-B polypeptide comprising an oxidant-resistant mutation at Cys405, Cys403, or Cys402. In some embodiments, the oxidant-resistant mutation is the substitution of a cysteine with an alanine, valine, leucine, or isoleucine. In some embodiments, the oxidant-resistant mutation at Cys405 is selected from: Cys405Ala; Cys405Val; Cys405Leu; and Cys405Ile. In some embodiments, the oxidant modification of ET-B Cys405, Cys403, or Cys402 comprises a disulfide bond or the formation of sulfenic acid.

In one aspect, described herein is a method of identifying an agent that reduces the level of oxidant-modified ET-B Cys405, Cys403, or Cys402, the method comprising contacting a cell expressing ET-B with a candidate agent and an oxidant measuring the level of oxidant-modification of ET-B Cys405, Cys403, or Cys402 wherein a lower level of oxidant-modification in the presence of the candidate agent indicates the agent is an agent that reduces the level of oxidant-modified ET-B Cys405, Cys403, or Cys402. In some embodiments, the oxidant modification of ET-B Cys405, Cys403, or Cys402 comprises a disulfide bond or the formation of sulfenic acid.

BRIEF DESCRIPTION OF THE DRAWINGS

FIG. 3A depicts a graph of the effect of spironolactone (SP)(25 mg/kg/d) on pulmonary vascular NO. levels in PAH assessed by measuring nitrite ($NO_2^-$) in lung tissue homogenates from Sprague-Dawley rats treated with vehicle control (V) or monocrotaline (MCT) (50 mg/kg) (*$p=0.05$, n=4). FIG. 3B depicts an image of tissue sections stained with anti-smooth muscle cell α-actin antibody. The number of muscularized distal pulmonary arterioles (red arrows) was counted in 20 consecutive fields per section (100× magnification). FIG. 3C depicts an image of Gomori's trichrome stain performed on paraffin-embedded lung sections. The perivascular collagen deposition in pulmonary arterioles measuring 20-50 μM located distal to terminal bronchioles (400× magnification) was measured. p<0.03 vs. V, *p<0.05 vs. MCT, n=4-5 rats per condition. Data are expressed as mean±S.E.M. Representative photomicrographs are shown.

FIG. 4A depicts a table of the data from a reversal study, in which Sprague-Dawley rats were randomized to receive vehicle control (V) or spironolactone (SP) (25 mg/kg/d) 14 days following the administration of V or monocrotaline (MCT) (50 mg/kg), and cardiopulmonary hemodynamics were assessed by cardiac catheterization 10 days later. *p<0.02 vs. MCT, n=6 rats per condition; **p<0.05 vs. V, n=4 rats per condition; #p<0.05 vs. MCT, n=4 rats per condition. FIG. 4B depicts a graph of the data from a prevention study, in which Sprague-Dawley rats were injected with SU-5416 and exposed to chronic hypoxia for 21 days. Immediately following exposure to hypoxia, rats were randomized to receive standard chow or eplerenone (0.6 gm/1 gm chow) until completion of the study. The effect of eplerenone on pulmonary artery systolic pressure (PASP) was assessed by cardiac catheterization. *p=0.048 vs. SU-5416/Hypoxia, n=5 rats per condition. HR, heart rate; CI, cardiac index; LVEDP, left ventricular end-diastolic pressure; PVRi, pulmonary vascular resistance index; SVRi, systemic vascular resistance index.

FIG. 5A depicts the effect of ET-1 on PGC-1α expression as assessed by Western analysis (n=4). FIG. 5B depicts the results of co-immunoprecipitation experiments which demonstrated that incubation of HPAECs with ET-1 (10 nM) for 24 h induced the association of PGC-1α with steroidogenesis factor-1 (SF) (n=3). FIG. 5C depicts a graph of chromatin immunoprecipitation (n=3) of cell lysates using antibodies to PGC-1α, SF, and immunoglobulin-G (IgG) as a negative control, followed by PCR amplification of the proximal region of the CYP11B2 promoter region containing the gonadotrope-specific element. FIG. 5D depicts a graph demonstrating the functional effect of PGC-1α stimulation on aldosterone production assessed in cells treated with the selective PGC-1α agonist pioglitazone (50 μM) for 24 h (n=4), or with ET-1 (10 nM) or angiotensin II (ANG)(10 μM) for 24 h as positive controls. *p<0.05 vs. V. PGC-1α, PPAR-γ co-activator-1α; arb. units, arbitrary units; IP, immunoprecipitation, IB; immunoblot. Data are presented as mean±S.E.M. Representative blots are shown.

FIGS. 6A-6D depict graphs and immunochemistry results demonstrating that aldosterone decreases $ET_B$-dependent synthesis of NO. FIG. 6A depicts a graph of $NO_2^-$ formation in HPAECs exposed to vehicle (V) or aldosterone (ALDO) ($10^{-7}$ mol/L) for 24 h in the presence or absence of spironolactone (SP) (10 μM). Prior to analysis, cells were exposed to ET-1 (10 nM) for 10 min to stimulate $ET_B$ signaling (n=4). FIG. 6B depicts a graph of the effect of ALDO on $ET_B$-dependent activation of eNOS (n=4). c.p.m., counts per minute. FIG. 6C depicts the effect of ALDO on $ET_B$-dependent NO. generation as measured by total NO. metabolite levels (NOx: $NO_2^- + NO_3^-$) (n=3). *p<0.05 vs. V, p<0.05 vs. ET-1, *p<0.05 vs. ET-1+ALDO. FIG. 6D depicts a western blot. HPAECs were exposed to V, hydrogen peroxide ($H_2O_2$) (200 μM) for 20 min, or ALDO ($10^{-7}$ mol/L) for 24 h to assess changes to the redox status and de novo disulfide bond formation by $ET_B$ cysteinyl thiols. For each disulfide formed, a 20-kDa shift in band location of the reduced $ET_B$ protein occurs on the Western blot using an antibody specific to the region of $ET_B$ containing Cys405 (n=4). Cyss, disulfide bond. A representative blot is shown. FIG. 6E depicts immunochemistry and the quantification thereof. The region of $ET_B$ containing Cys405 was immunoprecipitated from cells treated with V or ALDO ($10^{-7}$ mol/L) for 24 h and immunoblotting was performed to detect differences in protein sulfenic acid levels (R—SOH) (n=3). *p<0.05 vs. V. IP, immunoprecipitation, IB; immunoblot. Representative blots are shown. Data are presented as mean±S.E.M.

FIG. 7A depicts a western blot. COS-7 cells were transiently transected with wild type (WT)-eNOS and WT-$ET_B$ or mutant $ET_B$ DNA containing a substitution of alanine for cysteine at position 405 (C405A-$ET_B$) and protein expression was confirmed. No Tx, untransfected. FIG. 7B depicts a western blot. Disulfide bond formation was assessed by Western immunoblotting of PEG-conjugated maleimide-labeled cell extracts exposed to $H_2O_2$ (200 μmol/L for 20 min). Compared to WT-$ET_B$-transfected cells, in which $H_2O_2$ (200 μmol/L for 20 min) induced the formation of 1 or 2 disulfide bonds, C405A-$ET_B$ was resistant to disulfide bond formation (n=4) Cyss, disulfide bond. FIG. 7C depicts a graph. COS-7 cells expressing WT-eNOS and WT-$ET_B$ or C405A-$ET_B$ were exposed to vehicle (V) control or hydrogen peroxide ($H_2O_2$) (200 μmol/L) for 60 min. After that time, the cell culture medium was replaced and cells were treated with ET-1 (10 nM) for 10 min. and nitrite ($NO_2^-$) levels were measured (n=4). *p<0.002 vs. V-treated WT cells, **p<0.03 vs. $H_2O_2$-treated WT cells. Data are presented as mean±S.E.M. Representative blots are shown.

FIGS. 13A-13B depict western blotting and graphs demonstrating that ET-1 increases aldosterone synthase and aldosterone levels in HPAECs. FIG. 13A demonstrates that assessment of CYP11B2 (aldosterone synthase) protein expression by Western analysis in HPAECs exposed to vehicle control (V) or ET-1 (1, 10, 100 nM) for 24 h (*p<0.05 vs. V, n=3). FIG. 13B depicts a graph demonstrating the effect of ET-1 on aldosterone (ALDO) levels in the cell culture medium was assessed by EIA (*p<0.05 vs. V, n=4). A representative blot is shown.

FIG. 15A depicts a graph of hydrogen peroxide levels. HPAECs were exposed to vehicle control (V) or aldosterone (ALDO) ($10^{-7}$ mol/l) in the presence or absence of spironolactone (SP) (10 µM) for 24 h, and hydrogen peroxide ($H_2O_2$) levels were assessed by measuring Amplex Red fluorescence. (*p<0.05 vs. V, **p<0.05 vs. ALDO, n=3). To determine a potential source of $H_2O_2$ in ALDO ($10^{-9}$–$10^{-7}$ mol/l)-treated cells, Western analysis was performed to assess protein expression levels of (FIG. 15B) NOX4 and (FIG. 15C) the NOX4 subunit $p22^{phox}$. *p<0.05 vs. V, n=3. Data are presented as mean±S.E.M. Representative blots are shown.

FIG. 17A depicts a graph of $NO_2^-/NO_3^-$. HPAECs were treated with vehicle control (V) or aldosterone (ALDO) ($10^{-7}$ mol/l) for 24 h, and stimulated with ET-1 (10 nM) for 10 min immediately prior to measuring $NO_2^-/NO_3^-$. The contribution of ALDO to changes in $NO_2^-/NO_3^-$ was confirmed by co-incubation of ALDO-treated cells with spironolactone (SP)(10 µM). *p<0.04 vs. ALDO, n=3. FIG. 17B depicts immunochemistry and a graph of the quantification thereof. Peroxynitrite formation was assessed by 3-nitrotryosine immunohistochemistry. *p<0.05 vs. V, n=3. arb. units, arbitrary units.

DETAILED DESCRIPTION

Figures 1A, 1B, 1C, 1D:
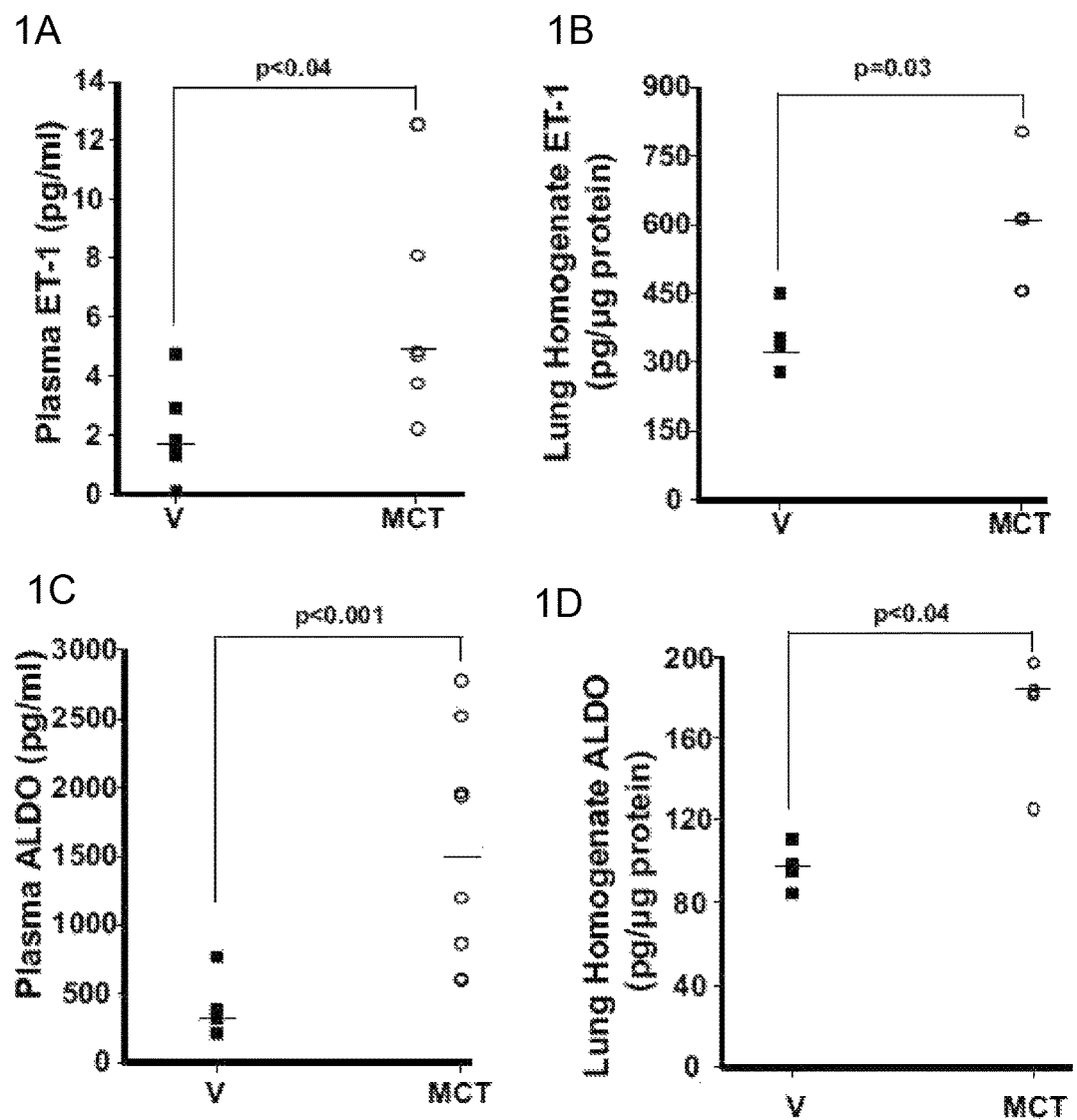
FIGS. 1A-1D depict graphs demonstrating that elevated levels of ET-1 are associated with hyperaldosteronism in PAH. The graphs depict levels of ET-1 (FIGS. 1A-1B) and aldosterone (ALDO) (FIGS. 1C-1D) measured in plasma and lung tissue homogenates of Sprague-Dawley rats 25 days following treatment with vehicle control (V) or monocrotaline (MCT) (50 mg/kg). (*$p<0.04$ vs. V, n=4-6 rats per treatment condition; **$p<0.001$ vs. V, n=6). Data are expressed as mean±S.E.M.

The production of nitric oxide is controlled, at least in part, by the activation of ET-B. As described herein, the inventors have discovered that ET-B activation and/or signaling activity is decreased by the oxidative modifications of cysteine residues of ET-B. Accordingly, provided herein are methods of increasing nitric oxide production and, e.g. treating hypertension, by administering an agent that reduces the level of oxidant-modified ET-B cysteine residues.

Hypertension, e.g. pulmonary arterial hypertension (PAH) is characterized, at least in part, by decreased endothelial nitric oxide (NO.) production and elevated levels of endothelin-1. Endothelin-1 is known to stimulate endothelial nitric oxide synthase (eNOS) via the endothelin-B receptor ($ET_B$ or ET-B). As demonstrated herein, the inventors have discovered that oxidants (e.g. reactive oxygen species (ROS)) modify certain residues on ET-B, thereby decreasing the ability of the receptor to trigger eNOS production in response to the presence of endothelin-1. The inventors have further demonstrated that by preventing or reducing these modifications of ET-B, eNOS production can be increased in subjects with hypertension.

As used herein, "ET-B", "$ET_B$", or "endothelin B receptor" refers to a G protein-couple receptor that is activated by binding to its ligand, endothelin. The sequence of ET-B for a number of species is well known in the art, e.g. human ET-B (e.g. NCBI Gene ID: 1910; SEQ ID NO: 6, NCBI Ref Seq: NM_000115 (mRNA) and SEQ ID NO: 7, NCBI Ref Seq NP_000106 (polypeptide)).

As described herein, the inventors have found that oxidants, e.g. ROS, can cause modifications of certain residues of ET-B, thereby impairing the function of ET-B. In some embodiments, the residues which can be subject to oxidant modification can include Cys402, Cys403, and/or Cys405, e.g. Cys402, Cys403, and/or Cys405 of a polypeptide having substantially the sequence of SEQ ID NO: 7. In some embodiments, one of the residues can be modified, e.g. one of Cys402, Cys403, and/or Cys405. In some embodiments, any combination of the three residues can be oxidatively modified. In some embodiment, all of the residues can be oxidatively modified. In some embodiments, the oxidant modification of ET-B Cys405, Cys403, or Cys402 can comprise a disulfide bond or the formation of sulfenic acid.

Aspects of the invention described herein relate to agents that reduce the level of oxidant-modified ET-B Cys405, Cys403, and/or Cys402.

As used herein, the term "agent that reduces the level of oxidant-modified ET-B Cys405, Cys403, and/or Cys402" refers to an agent which can decrease the level of onor or more of those residues that is oxidatively modified, e.g. by at least 10% or more, e.g. by 10% or more, 50% or more, 70% or more, 80% or more, 90% or more, 95% or more, or 98% or more. An agent that reduces the level of oxidant-modified ET-B Cys405, Cys403, and/or Cys402 can reduce the level of one or more of the Cys residues, e.g. one of the residues, two of the residues, or all three of the residues. The efficacy of agent that reduces the level of oxidant-modified ET-B Cys405, Cys403, and/or Cys402, e.g. its ability to decrease the level of oxidatively modified residues and/or to increase and/or potentiate the activity of ET-B can be determined, e.g. by measuring the level of modified residues. Methods for measuring the level of modified residues are known to one of skill in the art, e.g. immunoblotting to detect disulfide bond formation. An example of such a protocol is as follows: protein extracts from cells can be lysed in alkylating buffer containing 0.1 M Tris-HCL, pH 6.8, 1% SDS, 100 mM iodoacetamide, and 100 mM N-ethylmaleimide, and sonicated on ice for 5 min followed by a 30-min incubation at 25° C. Alkylated proteins can then be precipitated with acetone. Proteins are resuspended in 50 µl of 0.1 M Tris-HCl, pH 7.4, 1% SDS; and disulfides reduced with 5 mM tris(2-carboxyethyl)phosphine hydrochloride (TCEP). Following a 20-min incubation at 25° C., TCEP is removed with a Micro Bio-Spin™ column 6 (Bio-Rad), and 1% SDS is added to the eluant. The cysteines previously participating in a disulfide bond, now reduced, are labeled with 1 mM polyethylene glycol-conjugated maleimide (molecular mass 10 kDa) (Fluka). After a 1-h incubation at 25° C., proteins are precipitated with acetone, resuspended in 50 µl of non-reducing SDS electrophoresis buffer, and boiled for 10 min. Protein samples are then size-fractionated electrophoretically using SDS-PAGE, and transferred to a polyvinylidene fluoride membrane. The membrane can be immunoblotted with an anti-$ET_B$ antibody to the region of $ET_B$ that contains Cys405 (e.g. amino acid sequence to which $ET_B$ antibody was raised: clccwcqsfeekqsleekqsclkfkandhgydnfrssnkysss (SEQ ID NO: 1)) (Santa Cruz Biotechnology). Bands can be visualized using the ECL detection method.

The term "agent" refers generally to any entity which is normally not present or not present at the levels being administered to a cell, tissue or subject. An agent can be selected from a group including but not limited to: polynucleotides; polypeptides; small molecules; and antibodies or antigen-binding fragments thereof. A polynucleotide can be RNA or DNA, and can be single or double stranded, and can be selected from a group including, for example, nucleic acids and nucleic acid analogues that encode a polypeptide. A polypeptide can be, but is not limited to, a naturally-occurring polypeptide, a mutated polypeptide or a fragment thereof that retains the function of interest. Further examples of agents include, but are not limited to a nucleic acid aptamer, peptide-nucleic acid (PNA), locked nucleic acid (LNA), small organic or inorganic molecules; saccharide; oligosaccharides; polysaccharides; biological macromolecules, peptidomimetics; nucleic acid analogs and derivatives; extracts made from biological materials such as bacteria, plants, fungi, or mammalian cells or tissues and naturally occurring or synthetic compositions. An agent can be applied to the media, where it contacts the cell and induces its effects. Alternatively, an agent can be intracellular as a result of introduction of a nucleic acid sequence encoding the agent into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety selected, for example, from unsubstituted or substituted alkyl, aromatic, or heterocyclyl moieties including macrolides, leptomycins and related natural products or analogues thereof. Agents can be known to have a desired activity and/or property, or can be selected from a library of diverse compounds. As used herein, the term "small molecule" can refer to compounds that are "natural product-like," however, the term "small molecule" is not limited to "natural product-like" compounds. Rather, a small molecule is typically characterized in that it contains several carbon-carbon bonds, and has a molecular weight more than about 50, but less than about 5000 Daltons (5 kD). Preferably the small molecule has a molecular weight of less than 3 kD, still more preferably less than 2 kD, and most preferably less than 1 kD. In some cases it is preferred that a small molecule have a molecular mass equal to or less than 700 Daltons.

In some embodiments, an agent that reduces the level of oxidant-modified ET-B Cys405, Cys 403, and/or Cys402 can be an ET-B polypeptide comprising an oxidant-resistant mutation at Cys405, Cys403, or Cys402. In some embodiments, an agent that reduces the level of oxidant-modified ET-B Cys405, Cys 403, and/or Cys402 can be a nucleic acid encoding an ET-B polypeptide comprising an oxidant-resistant mutation at Cys405, Cys403, or Cys402.

In some embodiments, the mutation can be the replacement of the cysteine with, e.g. an alanine or other amino acid of similar size and polarity. In some embodiments the oxidant-resistant mutation can be the replacement of one or more of Cys405, Cys403, or Cys402 with alanine, valine, leucine, and isoleucine or a combination thereof. By way of non-limiting example, an ET-B polypeptide comprising an oxidant-resistant mutation at Cys405, Cys403, or Cys402 can have the following mutations: Cys405Ala and Cys402Ala; or Cys405Ala, Cys402Ile, and Cys403Val. Table 1 depicts exemplary embodiments of possible combinations of two oxidant-resistant mutations. It is specifically contemplated that any of the indicated embodiments in Table 1 can be combined with a third oxidant-resistant mutation as described herein.

TABLE 1

Exemplary embodiments of combinations of two oxidant-resistant mutations. X's mark embodiments of combinations of two oxidant-resistant mutations contemplated herein.

| | | Substitution of Cys402 with: | | | | Substitution of Cys403 with: | | | | Substitution of Cys405 with: | | | |
| --- | --- | --- | --- | --- | --- | --- | --- | --- | --- | --- | --- | --- | --- |
| | | Ala | Val | Leu | Ile | Ala | Val | Leu | Ile | Ala | Val | Leu | Ile |
| Substitution of Cys402 with: | Ala | | | | | X | X | X | X | X | X | X | X |
| | Val | | | | | X | X | X | X | X | X | X | X |
| | Leu | | | | | X | X | X | X | X | X | X | X |
| | Ile | | | | | X | X | X | X | X | X | X | X |
| Substitution of Cys403 with: | Ala | X | X | X | X | | | | | X | X | X | X |
| | Val | X | X | X | X | | | | | X | X | X | X |

TABLE 1-continued

Exemplary embodiments of combinations of two oxidant-resistant mutations. X's mark embodiments of combinations of two oxidant-resistant mutations contemplated herein.

| | | Substitution of Cys402 with: | | | | Substitution of Cys403 with: | | | | Substitution of Cys405 with: | | | |
|---|---|---|---|---|---|---|---|---|---|---|---|---|---|
| | | Ala | Val | Leu | Ile | Ala | Val | Leu | Ile | Ala | Val | Leu | Ile |
| | Leu | X | X | X | X | | | | | X | X | X | X |
| | Ile | X | X | X | X | | | | | X | X | X | X |
| Substitution of Cys405 with: | Ala | X | X | X | X | X | X | X | X | | | | |
| | Val | X | X | X | X | X | X | X | X | | | | |
| | Leu | X | X | X | X | X | X | X | X | | | | |
| | Ile | X | X | X | X | X | X | X | X | | | | |

In certain embodiments, ET-B polypeptides comprising an oxidant-resistant mutation at Cys405, Cys403, and/or Cys402 can themselves be administered, e.g., either directly, or more often, via expression from a nucleic acid construct. Such polypeptides will experience decreased levels of oxidant modifications at residues 402, 403, and/or 405 (e.g. residues 402, 403, and/or 405 of a polypeptide having the sequence of SEQ ID NO: 7) and therefore cause a reduction in the percentage of ET-B molecules in a given cell which have oxidant-modifications at residues 402, 403, and/or 405 (e.g. at Cys402, Cys403, and/or Cys405 or the equivalent residues). By reducing the level of oxidant modifications of Cys402, Cys403, and/or Cys405, the activity of ET-B is maintained, or, increased (or potentiated) relative to the activity of oxidized ET-B.

The ET-B polypeptide comprising an oxidant-resistant mutation at Cys405, Cys403, and/or Cys402 can have the sequence of SEQ ID NO: 7 with any of the mutations described herein at residues 402, 403, and/or 405. The ET-B polypeptides comprising an oxidant-resistant mutation at Cys405, Cys403, and/or Cys402 can further comprise additional mutations and/or modifications. For example, one of ordinary skill in the art will recognize that sequence differences will exist due to allelic variation, and will also recognize that other animals, particularly other mammals, have corresponding ET-B polypeptides, which have been identified or can be readily identified using sequence alignment and confirmation of activity.

ET-B is known to comprise a long extracellular domain, 7 transmembrane domains, 3 extracellular loops, 3 intracellular loops, and a cytoplasmic C-terminal domain. The transmembrane domains I-III and VII and the extracellular loops comprise the agonist binding domain and the C-terminal tail is responsible for signaling activity once activated by binding of endothelin 1. A number of phosphorylation sites are believed to contribute to activity. The structure of ET-B is discussed in further detail, e.g. in Mazzuca and Khali. Biochemical Pharmacology 2012 84:147-162; which is incorporated by reference herein in its entirety.

At a minimum, a "ET-B polypeptide" as the term is used herein, can bind endothelin 1 and induce production of nitric oxide in endothelial cells. Methods for detecting nitric oxide levels are known in the art and described in the Examples herein. An ET-B polypeptide can include conservative substitution variants of a mammalian ET-B polypeptide that maintain the ability to bind endothelin 1 and induce production of nitric oxide in endothelial cells. ET-B variants can be obtained by mutations of native ET-B nucleotide sequences, for example. The domain structures as known in the art and as described herein provides guidance to one of ordinary skill in the art for the regions of ET-B polypeptides that will tolerate modification yet likely to retain ET-B activity. A "ET-B variant," as referred to herein, is a polypeptide substantially homologous to a native ET-B, but which has an amino acid sequence different from that of native ET-B because of one or a limited number of deletions, insertions or substitutions. One of ordinary skill in the art will recognize that modifications can be introduced in a ET-B sequence without destroying ET-B activity. Such modified ET-B's can also be used in the methods described herein, e.g., if the modifications do not alter the ability to bind endothelin 1 and induce production of nitric oxide in endothelial cells relative to wild-type ET-B.

The variant amino acid or DNA sequence preferably is at least 90%, at least 91%, at least 92%, at least 93%, at least 94%, at least 95%, at least 96%, at least 97%, at least 98%, at least 99%, or more, identical to a native ET-B sequence. The degree of homology (percent identity) between a native and a mutant sequence can be determined, for example, by comparing the two sequences using freely available computer programs commonly employed for this purpose on the world wide web.

Variants can comprise conservatively substituted sequences, meaning that one or more amino acid residues of a native ET-B polypeptide are replaced by a residue having similar physiochemical characteristics, e.g., substituting one aliphatic residue for another (such as Ile, Val, Leu, or Ala for one another), or substitution of one polar residue for another (such as between Lys and Arg; Glu and Asp; or Gln and Asn). Other such conservative substitutions, e.g., substitutions of entire regions having similar hydrophobicity characteristics, are well known. ET-B polypeptides comprising conservative amino acid substitutions can be tested in any one of the assays described herein to confirm that a desired activity of a ET-B polypeptide is retained. By "retained" is meant that the activity is at least 50% of that of the wild-type polypeptide, preferably at least 60%, at least 70%, at least 80%, at least 90%, at least 100%, at least 150%, at least 200%, at least 300% or more, relative to wild-type.

Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Examples of conservative substitutions for use in the PPARγ2 variants described herein are as follows: Ala into Gly or into Ser; Arg into Lys; Asn into Gln or into His; Asp into Glu; Cys into Ser; Gln into Asn; Glu into Asp; Gly into Ala or into Pro; His into Asn or into Gln; Ile into Leu or into Val; Leu into Ile or into Val; Lys into Arg, into Gln or into Glu; Met into Leu, into Tyr or into Ile; Phe into Met, into Leu or into Tyr; Ser into Thr; Thr into Ser; Trp into Tyr; Tyr into Trp; and/or Phe into Val, into Ile or into Leu.

Alterations of the native amino acid sequence can be accomplished by any of a number of known recombinant DNA techniques are widely used in the art.

In some embodiments, an agent that can decrease the level of oxidant modifications of Cys405, Cys403, and/or Cys402 of ET-B can be a nucleic acid encoding an ET-B polypeptide comprising an oxidant-resistant mutation at Cys405, Cys403, and/or Cys402 as described herein above. In some embodiments, the nucleic acid encoding an ET-B polypeptide comprising an oxidant-resistant mutation at Cys405, Cys403, and/or Cys402 can have the sequence of SEQ ID NO: 6 comprising one or more mutations that result in an oxidant-resistant mutation at Cys405, Cys403, and/or Cys402 or can be a homologous nucleic acid with a sequence identity of, for example, at least at least 90%, 95%, 99%, or even 100%, over a region spanning 50, 100,150, 200,250,300,350,400, 450, 500, or even more nucleotides. One of ordinary skill in the art will also recognize that modifications can be introduced in a ET-B sequence without destroying ET-B activity. Such modified ET-B's can also be used in the present invention, e.g., if the modifications do not substantially reduce the ability of the ET-B polypeptide to bind endothelin 1 and induce eNOS production. A homologous polypeptide can be a peptide with a sequence identity of, for example, at least 90%, 95%, 99%, or even 100%, over a region spanning 50, 100,150, 200,250,300,350,400, 450, 500, or even more amino acids as compared to a ET-B polypeptide as described above herein.

The agent can comprise a vector. Many vectors useful for transferring exogenous genes into target mammalian cells are available. The vectors can be episomal, e.g., plasmids, virus derived vectors such cytomegalovirus, adenovirus, etc., or can be integrated into the target cell genome, through homologous recombination or random integration, e.g., retrovirus derived vectors such MMLV, HIV-1, ALV, etc. Many viral vectors are known in the art and can be used as carriers of a nucleic acid modulatory compound into the cell. For example, constructs containing the nucleic acid encoding a polypeptide can be integrated and packaged into non-replicating, defective viral genomes like Adenovirus, Adeno-associated virus (AAV), or Herpes simplex virus (HSV) or others, including retroviral and lentiviral vectors, for infection or transduction into cells. Alternatively, the construct can be incorporated into vectors capable of episomal replication, e.g. EPV and EBV vectors. The nucleic acid incorporated into the vector can be operatively linked to an expression control sequence such that the expression control sequence controls and regulates the transcription and translation of that polynucleotide sequence.

Agents comprising a nucleic acid, as described herein, can be delivered to a cell using a viral vector. Retroviruses, such as lentiviruses, provide a convenient platform for delivery of nucleic acid sequences encoding an agent of interest. A selected nucleic acid sequence can be inserted into a vector and packaged in retroviral particles using techniques known in the art. The recombinant virus can then be isolated and delivered to cells, e.g. in vitro or ex vivo. Retroviral systems are well known in the art and are described in, for example, U.S. Pat. No. 5,219,740; Kurth and Bannert (2010) "Retroviruses: Molecular Biology, Genomics and Pathogenesis" Calster Academic Press (ISBN:978-1-90455-55-4); and Hu and Pathak Pharmacological Reviews 2000 52:493-512; which are incorporated by reference herein in their entirety.

In some embodiments, a nucleotide sequence encoding an agent of interest is inserted into an adenovirus-based expression vector. Unlike retroviruses, which integrate into the host genome, adenoviruses persist extrachromosomally thus minimizing the risks associated with insertional mutagenesis (Haj-Ahmad and Graham (1986) J. Virol. 57:267-74; Bett et al. (1993) J. Virol. 67:5911-21; Mittereder et al. (1994) Human Gene Therapy 5:717-29; Seth et al. (1994) J. Virol. 68:933-40; Barr et al. (1994) Gene Therapy 1:51-58; Berkner, K. L. (1988) BioTechniques 6:616-29; and Rich et al. (1993) Human Gene Therapy 4:461-76). Adenoviral vectors have several advantages in gene therapy. They infect a wide variety of cells, have a broad host-range, exhibit high efficiencies of infectivity, direct expression of heterologous sequences at high levels, and achieve long-term expression of those sequences in vivo. The virus is fully infective as a cell-free virion so injection of producer cell lines is not necessary. With regard to safety, adenovirus is not associated with severe human pathology, and the recombinant vectors derived from the virus can be rendered replication defective by deletions in the early-region 1 ("E1") of the viral genome. Adenovirus can also be produced in large quantities with relative ease. For all these reasons vectors derived from human adenoviruses, in which at least the E1 region has been deleted and replaced by a gene of interest, have been used extensively for gene therapy experiments in the pre-clinical and clinical phase.

Adenoviral vectors for use with the compositions and methods described herein can be derived from any of the various adenoviral serotypes, including, without limitation, any of the over 40 serotype strains of adenovirus, such as serotypes 2, 5, 12, 40, and 41. The adenoviral vectors of used in the methods described herein are generally replication-deficient and contain the sequence of interest under the control of a suitable promoter. For example, U.S. Pat. No. 6,048,551, incorporated herein by reference in its entirety, describes replication-deficient adenoviral vectors that include a human gene under the control of the Rous Sarcoma Virus (RSV) promoter. Other recombinant adenoviruses of various serotypes, and comprising different promoter systems, can be created by those skilled in the art. See, e.g., U.S. Pat. No. 6,306,652, incorporated herein by reference in its entirety.

Other useful adenovirus-based vectors for delivery of nucleic acid sequence encoding an ET-B comprising an oxidant-resistant mutation at Cys405, Cys403, and/or Cys402 include, but are not limited to: "minimal" adenovirus vectors as described in U.S. Pat. No. 6,306,652, which retain at least a portion of the viral genome required for encapsidation (the encapsidation signal), as well as at least one copy of at least a functional part or a derivative of the ITR; and the "gutless" (helper-dependent) adenovirus in which the vast majority of the viral genome has been removed and which produce essentially no viral proteins, such vectors can permit gene expression to persist for over a year after a single administration (Wu et al. (2001)

Anesthes. 94:1119-32; Parks (2000) Clin. Genet. 58:1-11; Tsai et al. (2000) Curr. Opin. Mol. Ther. 2:515-23).

In some embodiments, a nucleotide sequence encoding an ET-B polypeptide comprising an oxidant-resistant mutation at Cys405, Cys403, and/or Cys402 can be inserted into an adeno-associated virus-based expression vector. AAV is a parvovirus which belongs to the genus *Dependovirus* and has several features not found in other viruses. AAV can infect a wide range of host cells, including non-dividing cells. AAV can infect cells from different species. AAV has not been associated with any human or animal disease and does not appear to alter the biological properties of the host cell upon integration. Indeed, it is estimated that 80-85% of the human population has been exposed to the virus. Finally, AAV is stable at a wide range of physical and chemical conditions, facilitating production, storage and transportation.

AAV is a helper-dependent virus; that is, it requires co-infection with a helper virus (e.g., adenovirus, herpesvirus or vaccinia) in order to form AAV virions in the wild. In the absence of co-infection with a helper virus, AAV establishes a latent state in which the viral genome inserts into a host cell chromosome, but infectious virions are not produced. Subsequent infection by a helper virus rescues the integrated genome, allowing it to replicate and package its genome into infectious AAV virions. While AAV can infect cells from different species, the helper virus must be of the same species as the host cell. Thus, for example, human AAV will replicate in canine cells co-infected with a canine adenovirus.

Adeno-associated virus (AAV) has been used with success in gene therapy. AAV has been engineered to deliver genes of interest by deleting the internal nonrepeating portion of the AAV genome (i.e., the rep and cap genes) and inserting a heterologous sequence (in this case, the sequence encoding the agent) between the ITRs. The heterologous sequence is typically functionally linked to a heterologous promoter (constitutive, cell-specific, or inducible) capable of driving expression in the patient's target cells under appropriate conditions.

Recombinant AAV virions comprising a nucleic acid sequence encoding an agent of interest can be produced using a variety of art-recognized techniques, as described in U.S. Pat. Nos. 5,139,941; 5,622,856; 5,139,941; 6,001,650; and 6,004,797, the contents of each of which are incorporated by reference herein in their entireties. Vectors and cell lines necessary for preparing helper virus-free rAAV stocks are commercially available as the AAV Helper-Free System (Catalog No. 240071) (Agilent Technologies, Santa Clara, Calif.).

Additional viral vectors useful for delivering nucleic acid molecules encoding an ET-B polypeptide comprising an oxidant-resistant mutation at Cys405, Cys403, and/or Cys402 include those derived from the pox family of viruses, including vaccinia virus and avian poxvirus. Alternatively, avipoxviruses, such as the fowlpox and canarypox viruses, can be used to deliver the genes. The use of avipox vectors in cells of human and other mammalian species is advantageous with regard to safety because members of the avipox genus can only productively replicate in susceptible avian species. Methods for producing recombinant avipoxviruses are known in the art and employ genetic recombination, see, e.g., WO 91/12882; WO 89/03429; and WO 92/03545.

Molecular conjugate vectors, such as the adenovirus chimeric vectors, can also be used for delivery of sequence encoding an ET-B polypeptide comprising an oxidant-resistant mutation at Cys405, Cys403, and/or Cys402 (Michael et al. (1993) J. Biol. Chem. 268:6866-69 and Wagner et al. (1992) Proc. Natl. Acad. Sci. USA 89:6099-6103). Members of the *Alphavirus* genus, for example the Sindbis and Semliki Forest viruses, can also be used as viral vectors for delivering a nucleic acid sequence (See, e.g., Dubensky et al. (1996) J. Virol. 70:508-19; WO 95/07995; WO 96/17072).

Administration of an agent that reduces the level of oxidant-modified ET-B Cys405, Cys403, or Cys402 can increase the level of ET-B activity and/or potentiate ET-B to be responsive to activation. Accordingly, in one aspect, provided herein is a method of potentiating or increasing nitric oxide vasodilatory signaling activity, the method comprising administering an agent that reduces the level of oxidant-modified ET-B Cys405, Cys403, or Cys402.

Increases in endothelial nitric oxide levels can cause vasodilation, reducing the symptoms of hypertension. Accordingly, in one aspect, the invention described herein relates to methods of treating hypertension in a subject in need thereof, the method comprising administering an agent that reduces the level of oxidant-modified ET-B Cys405, Cys403, or Cys402. In some embodiments, the hypertension can be systemic hypertension, e.g. "high blood pressure." In some embodiments the hypertension can be pulmonary arterial hypertension. In some embodiments, a subject treated in accordance with the methods described herein can be a subject in need of treatment for systemic hypertension and/or pulmonary arterial hypertension.

As used herein, "hypertension" refers to abnormally high blood pressure, e.g. beyond the upper value of the normal range. Hypertension can be "essential" or "secondary." As used herein, the term "essential hypertension" refers to essential primary or idiopathic hypertension which is a systemic hypertension of an unknown cause. Essential hypertension is the cause of 95% of all cases of hypertension diagnosed. It includes hypertension of all grades, including borderline, mild moderate and severe. It also includes hypertensive urgencies and emergencies or hypertensive crises, and indeed all cases of hypertension where there is not a known cause. As used herein, the term "secondary hypertension" refers to systemic hypertension of a known and reversible cause. Secondary causes are largely those due to renal or renal artery diseases or endocrine disorders. These account for fewer than 2-10% of the diagnosed cases of hypertension.

As used herein, "pulmonary arterial hypertension" or "PAH" refers to vascoconstruction of blood vessels connected to and within the lungs. PAH leads to hypertrophy of the right ventricle and/or right heart failure. A diagnosis of PAH typically involves pressure measurements with a Swan-Ganze catheter through the right side of the heart or estimates via echocardiogram.

In some embodiments, the methods described herein relate to treating a subject having or diagnosed as having hypertension with an agent that reduces the level of oxidant-modified ET-B Cys405, Cys403, or Cys402. Subjects having hypertension can be identified by a physician using current methods of diagnosing hypertension and/or PAH. Symptoms and/or complications of hypertension which characterize these conditions and aid in diagnosis are well known in the art and include but are not limited to, shortness of breath, fatigue, non-productive cough, angina pectoris, fainting, syncope, peripheral edema, hemoptysis. Pulmonary venous hypertension typically presents with shortness of breath while lying flat or sleeping, while PAH typically does not. Tests that may aid in a diagnosis of, e.g. hypertension include, but are not limited to, physical examination for loud S2 (pulmonic valve closure sound), (para)sternal heave, jugular venous distension, pedal edeman, ascites, hepatojugular reflex; pulmonary function tests; chest x-rays and/or CT scans, etc. A family history of hypertension, or exposure to risk factors for hypertension (e.g. exposure to cocaine, methamphetamine, alcohol, or tobacco) can also aid in determining if a subject is likely to have hypertension or in making a diagnosis of hypertension.

The compositions and methods described herein can be administered to a subject having or diagnosed as having hypertension. In some embodiments, the methods described herein comprise administering an effective amount of compositions described herein, e.g. an agent that reduces the level of oxidant-modified ET-B Cys405, Cys403, or Cys402 to a subject in order to alleviate a symptom of hypertension. As used herein, "alleviating a symptom of hypertension" is ameliorating any condition or symptom associated with hypertension. As compared with an equivalent untreated control, such reduction is by at least 5%, 10%, 20%, 40%, 50%, 60%, 80%, 90%, 95%, 99% or more as measured by any standard technique. A variety of means for administering the compositions described herein to subjects are known to those of skill in the art. Such methods can include, but are not limited to oral, parenteral, intravenous, intramuscular, subcutaneous, transdermal, airway (aerosol), pulmonary, cutaneous, injection, or topical administration. Administration can be local or systemic.

The term "effective amount" as used herein refers to the amount of an agent that reduces the level of oxidant-modified ET-B Cys405, Cys403, or Cys402 needed to alleviate at least one or more symptom of the disease or disorder, and relates to a sufficient amount of pharmacological composition to provide the desired effect. The term "therapeutically effective amount" therefore refers to an amount of an agent that reduces the level of oxidant-modified ET-B Cys405, Cys403, or Cys402 that is sufficient to provide a particular anti-hypertensive effect when administered to a typical subject. An effective amount as used herein, in various contexts, would also include an amount sufficient to delay the development of a symptom of the disease, alter the course of a symptom disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the LD50 (the dose lethal to 50% of the population) and the ED50 (the dose therapeutically effective in 50% of the population). The dosage can vary depending upon the dosage form employed and the route of administration utilized. The dose ratio between toxic and therapeutic effects is the therapeutic index and can be expressed as the ratio LD50/ED50. Compositions and methods that exhibit large therapeutic indices are preferred. A therapeutically effective dose can be estimated initially from cell culture assays. Also, a dose can be formulated in animal models to achieve a circulating plasma concentration range that includes the IC50 (i.e., the concentration of an agent that reduces the level of oxidant-modified ET-B Cys405, Cys403, or Cys402, which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay, e.g., assay for nitric oxide levels, among others. The dosage can be determined by a physician and adjusted, as necessary, to suit observed effects of the treatment.

In some embodiments, the technology described herein relates to a pharmaceutical composition comprising an agent that reduces the level of oxidant-modified ET-B Cys405, Cys403, or Cys402 as described herein, and optionally a pharmaceutically acceptable carrier. Pharmaceutically acceptable carriers and diluents include saline, aqueous buffer solutions, solvents and/or dispersion media. The use of such carriers and diluents is well known in the art. Some non-limiting examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) $C_2$-$C_{12}$ alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein. In some embodiments, the carrier inhibits the degradation of the active agent, e.g. an agent that reduces the level of oxidant-modified ET-B Cys405, Cys403, or Cys402 as described herein.

In some embodiments, the pharmaceutical composition comprising an agent that reduces the level of oxidant-modified ET-B Cys405, Cys403, or Cys402 as described herein can be a parenteral dose form. Since administration of parenteral dosage forms typically bypasses the patient's natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. In addition, controlled-release parenteral dosage forms can be prepared for administration of a patient, including, but not limited to, DUROS®-type dosage forms and dose-dumping.

Suitable vehicles that can be used to provide parenteral dosage forms of an agent that reduces the level of oxidant-modified ET-B Cys405, Cys403, or Cys402 as disclosed within are well known to those skilled in the art. Examples include, without limitation: sterile water; water for injection USP; saline solution; glucose solution; aqueous vehicles such as but not limited to, sodium chloride injection, Ringer's injection, dextrose Injection, dextrose and sodium chloride injection, and lactated Ringer's injection; water-miscible vehicles such as, but not limited to, ethyl alcohol, polyethylene glycol, and propylene glycol; and non-aqueous vehicles such as, but not limited to, corn oil, cottonseed oil, peanut oil, sesame oil, ethyl oleate, isopropyl myristate, and benzyl benzoate. Compounds that alter or modify the solubility of a pharmaceutically acceptable salt of an agent that reduces the level of oxidant-modified ET-B Cys405, Cys403, or Cys402 as disclosed herein can also be incorporated into the parenteral dosage forms of the disclosure, including conventional and controlled-release parenteral dosage forms.

Pharmaceutical compositions comprising an agent that reduces the level of oxidant-modified ET-B Cys405, Cys403, or Cys402 can also be formulated to be suitable for oral administration, for example as discrete dosage forms, such as, but not limited to, tablets (including without limitation scored or coated tablets), pills, caplets, capsules, chewable tablets, powder packets, cachets, troches, wafers, aerosol sprays, or liquids, such as but not limited to, syrups, elixirs, solutions or suspensions in an aqueous liquid, a non-aqueous liquid, an oil-in-water emulsion, or a water-in-oil emulsion. Such compositions contain a predetermined amount of the pharmaceutically acceptable salt of the disclosed compounds, and may be prepared by methods of pharmacy well known to those skilled in the art. See generally, Remington: The Science and Practice of Pharmacy, 21st Ed., Lippincott, Williams, and Wilkins, Philadelphia Pa. (2005).

Conventional dosage forms generally provide rapid or immediate drug release from the formulation. Depending on the pharmacology and pharmacokinetics of the drug, use of conventional dosage forms can lead to wide fluctuations in the concentrations of the drug in a patient's blood and other tissues. These fluctuations can impact a number of parameters, such as dose frequency, onset of action, duration of efficacy, maintenance of therapeutic blood levels, toxicity, side effects, and the like. Advantageously, controlled-release formulations can be used to control a drug's onset of action, duration of action, plasma levels within the therapeutic window, and peak blood levels. In particular, controlled- or extended-release dosage forms or formulations can be used to ensure that the maximum effectiveness of a drug is achieved while minimizing potential adverse effects and safety concerns, which can occur both from under-dosing a drug (i.e., going below the minimum therapeutic levels) as well as exceeding the toxicity level for the drug. In some embodiments, the agent that reduces the level of oxidant-modified ET-B Cys405, Cys403, or Cys402 can be administered in a sustained release formulation.

Controlled-release pharmaceutical products have a common goal of improving drug therapy over that achieved by their non-controlled release counterparts. Ideally, the use of an optimally designed controlled-release preparation in medical treatment is characterized by a minimum of drug substance being employed to cure or control the condition in a minimum amount of time. Advantages of controlled-release formulations include: 1) extended activity of the drug; 2) reduced dosage frequency; 3) increased patient compliance; 4) usage of less total drug; 5) reduction in local or systemic side effects; 6) minimization of drug accumulation; 7) reduction in blood level fluctuations; 8) improvement in efficacy of treatment; 9) reduction of potentiation or loss of drug activity; and 10) improvement in speed of control of diseases or conditions. Kim, Cherng-ju, Controlled Release Dosage Form Design, 2 (Technomic Publishing, Lancaster, Pa.: 2000).

Most controlled-release formulations are designed to initially release an amount of drug (active ingredient) that promptly produces the desired therapeutic effect, and gradually and continually release other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, ionic strength, osmotic pressure, temperature, enzymes, water, and other physiological conditions or compounds.

A variety of known controlled- or extended-release dosage forms, formulations, and devices can be adapted for use with the salts and compositions of the disclosure. Examples include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,733,566; and 6,365,185 B1; each of which is incorporated herein by reference. These dosage forms can be used to provide slow or controlled-release of one or more active ingredients using, for example, hydroxypropylmethyl cellulose, other polymer matrices, gels, permeable membranes, osmotic systems (such as OROS® (Alza Corporation, Mountain View, Calif. USA)), or a combination thereof to provide the desired release profile in varying proportions.

The methods described herein can further comprise administering a second agent and/or treatment to the subject, e.g. as part of a combinatorial therapy. Non-limiting examples of a second agent and/or treatment can include diuretics, beta blockers (e.g. atenolol, metoprolol, nadolol, nebivolol, oxprenolol, pindolol, propranolol, and timolol), and/or ACE inhibitors (e.g. captopril, enalapril, fosinopril, lisinopril, perindopril, quinapril, ramipril, trandolapril, and benazepril).

PAH can also be treated with, e.g. lifestyle changes, digoxin, diuretics (e.g. amiloride, triamterene, spironolactone, metolazone, chlorthalidone, indapadmide, bendroflumethiazide, epitizide, torsemide, furosemide, ethacrynic acid, and bumetanide), oral anticoagulants, prostaglandins (e.g. prostacyclin, epoprostenol, treprostinil, iloprost, and beraprost), phosphodiesterase type 5 inhibitors (e.g. sildenafil and tadalafil), and/or oxygen therapy. Surgical treatments for PAH can include atrial septostomy, lung transplantation, and/or pulmonary thromboendarterectomy.

In certain embodiments, an effective dose of a composition comprising an agent that reduces the level of oxidant-modified ET-B Cys405, Cys403, or Cys402 as described herein can be administered to a patient once. In certain embodiments, an effective dose of a composition comprising an agent that reduces the level of oxidant-modified ET-B Cys405, Cys403, or Cys402 can be administered to a patient repeatedly. For systemic administration, subjects can be administered a therapeutic amount of a composition comprising an agent that reduces the level of oxidant-modified ET-B Cys405, Cys403, or Cys402, such as, e.g. 0.1 mg/kg, 0.5 mg/kg, 1.0 mg/kg, 2.0 mg/kg, 2.5 mg/kg, 5 mg/kg, 10 mg/kg, 15 mg/kg, 20 mg/kg, 25 mg/kg, 30 mg/kg, 40 mg/kg, 50 mg/kg, or more.

In some embodiments, after an initial treatment regimen, the treatments can be administered on a less frequent basis. For example, after treatment biweekly for three months, treatment can be repeated once per month, for six months or a year or longer. Treatment according to the methods described herein can reduce levels of a marker or symptom of a condition, e.g. blood pressure by at least 10%, at least 15%, at least 20%, at least 25%, at least 30%, at least 40%, at least 50%, at least 60%, at least 70%, at least 80% or at least 90% or more.

The dosage of a composition as described herein can be determined by a physician and adjusted, as necessary, to suit observed effects of the treatment. With respect to duration and frequency of treatment, it is typical for skilled clinicians to monitor subjects in order to determine when the treatment is providing therapeutic benefit, and to determine whether to increase or decrease dosage, increase or decrease administration frequency, discontinue treatment, resume treatment, or make other alterations to the treatment regimen. The dosing schedule can vary from once a week to daily depending on a number of clinical factors, such as the subject's sensitivity to an agent that reduces the level of oxidant-modified ET-B Cys405, Cys403, or Cys402. The desired dose or amount of activation can be administered at one time or divided into subdoses, e.g., 2-4 subdoses and administered over a period of time, e.g., at appropriate intervals through the day or other appropriate schedule. In some embodiments, administration can be chronic, e.g., one or more doses and/or treatments daily over a period of weeks or months. Examples of dosing and/or treatment schedules are administration daily, twice daily, three times daily or four or more times daily over a period of 1 week, 2 weeks, 3 weeks, 4 weeks, 1 month, 2 months, 3 months, 4 months, 5 months, or 6 months, or more. A composition comprising an agent that reduces the level of oxidant-modified ET-B Cys405, Cys403, or Cys402 can be administered over a period of time, such as over a 5 minute, 10 minute, 15 minute, 20 minute, or 25 minute period.

The dosage ranges for the administration of an agent that reduces the level of oxidant-modified ET-B Cys405, Cys403, or Cys402, according to the methods described herein depend upon, for example, the form of the agent that reduces the level of oxidant-modified ET-B Cys405, Cys403, or Cys402 its potency, and the extent to which symptoms, markers, or indicators of a condition described herein are desired to be reduced, for example the percentage reduction desired for hypertension or the extent to which, for example, nitric oxide levels are desired to be induced. The dosage should not be so large as to cause adverse side effects, such as dangerously or abnormally low blood pressure. Generally, the dosage will vary with the age, condition, and sex of the patient and can be determined by one of skill in the art. The dosage can also be adjusted by the individual physician in the event of any complication.

The efficacy of an agent that reduces the level of oxidant-modified ET-B Cys405, Cys403, or Cys402 in, e.g. the treatment of a condition described herein, or to induce a response as described herein (e.g. a reduction in hypertension) can be determined by the skilled clinician. However, a treatment is considered "effective treatment," as the term is used herein, if one or more of the signs or symptoms of a condition described herein are altered in a beneficial manner, other clinically accepted symptoms are improved, or even ameliorated, or a desired response is induced e.g., by at least 10% following treatment according to the methods described herein. Efficacy can be assessed, for example, by measuring a marker, indicator, symptom, and/or the incidence of a condition treated according to the methods described herein or any other measurable parameter appropriate, e.g. blood pressure. Efficacy can also be measured by a failure of an individual to worsen as assessed by hospitalization, or need for medical interventions (i.e., progression of the disease is halted). Methods of measuring these indicators are known to those of skill in the art and/or are described herein. Treatment includes any treatment of a disease in an individual or an animal (some non-limiting examples include a human or an animal) and includes: (1) inhibiting the disease, e.g., preventing a worsening of symptoms (e.g. pain or inflammation); or (2) relieving the severity of the disease, e.g., causing regression of symptoms. An effective amount for the treatment of a disease means that amount which, when administered to a subject in need thereof, is sufficient to result in effective treatment as that term is defined herein, for that disease. Efficacy of an agent can be determined by assessing physical indicators of a condition or desired response, (e.g. a decrease in blood pressure). It is well within the ability of one skilled in the art to monitor efficacy of administration and/or treatment by measuring any one of such parameters, or any combination of parameters. Efficacy can be assessed in animal models of a condition described herein, for example treatment of hypertension in animal models. When using an experimental animal model, efficacy of treatment is evidenced when a statistically significant change in a marker is observed, e.g. blood pressure and/or nitric oxide levels.

In vitro and animal model assays are provided herein which allow the assessment of a given dose of an agent that reduces the level of oxidant-modified ET-B Cys405, Cys403, or Cys402. By way of non-limiting example, the effects of a dose of an agent that reduces the level of oxidant-modified ET-B Cys405, Cys403, or Cys402 can be assessed by measuring eNOS activity in cultured cells. A non-limiting example of a protocol for such an assay using a NOS Activity Kit (Cat No. 781001; Cayman, Ann Arbor, Mich.) is as follows: cells are washed with PBS containing 1 mM EDTA, transferred to a microcentrifuge tube, and centrifuged at 14,000×g at 4° C. for 2 min. The supernatant is decanted and homogenization buffer (250 mM Tris-HCl, pH 7.4, 6 µM BH$_4$, 2 µM flavin adenine dinucleotide, and 2 µM flavin adenine mononucleotide) is added to the cell pellets. The cells are lysed and exposed to [$^{14}$C] arginine (100 µCi/ml) for 2 min prior to incubation with ET-1 (10 nM) or PBS as vehicle control for 30 min at room 25° C. The samples are then centrifuged at 14,000×g for 30 seconds and radioactivity of the eluant quantified in a liquid scintillation counter.

The efficacy of a given dosage can also be assessed in an animal model, e.g. the monocrontaline model of PAH. For example, rats can be fed standard chow and treated with a 0.5 ml intraperitoneal injection of MCT (50 mg/ml) (Sigma-Aldrich) or 0.9% saline as control. Rats are administered a dosage of an agent as described herein and hemodynamic and tissue analyses were performed.

In one aspect, provided herein is a method of identifying an agent that reduces the level of oxidant-modified ET-B Cys405, Cys403, or Cys402, the method comprising contacting a cell expressing ET-B with a candidate agent and an oxidant and measuring the level of oxidant-modification of ET-B Cys405, Cys403, or Cys402; wherein a lower level of oxidant-modification in the presence of the candidate agent indicates the agent is an agent that reduces the level of oxidant-modified ET-B Cys405, Cys403, or Cys402. In some embodiments, the method of claim 12, wherein the oxidant modification of ET-B Cys405, Cys403, or Cys402 comprises a disulfide bond or the formation of sulfenic acid.

As described herein, the inventors have identified that agents which reduce the level of oxidant modification of ET-B Cys405, Cys403, and/or Cys402 can, e.g. increase vasoactive signaling, increase nitric oxide production, and/or be used to treat, e.g. hypertension. Accordingly, some embodiments of the invention are generally related to assays, methods and systems for indentifying an agent that reduces the level of oxidant-modified ET-B Cys405, Cys403, or Cys402. In some embodiments, the method comprises contacting a cell expressing ET-B with a candidate agent and an oxidant; measuring the level of oxidant-modification of ET-B Cys405, Cys403, or Cys402; wherein a lower level of oxidant-modification in the presence of the candidate agent indicates the agent is an agent that reduces the level of oxidant-modified ET-B Cys405, Cys403, or Cys402. In some embodiments, the oxidant modification of ET-B Cys405, Cys403, or Cys402 can comprise a disulfide bond or the formation of sulfenic acid.

The presence and/or level of an oxidant modification can be determined as describe elsewhere herein.

In some embodiments, the cell can be an endothelial cell. In some embodiments, the cell can be a cell transformed with an expression vector that allows expression of ET-B in that cell. The candidate agent can be an agent as define elsewhere herein. In some embodiments, the candidate agent can be an aptamers or a small molecule. In some embodiments, the candidate agent is part of a library of candidate agents.

For convenience, the meaning of some terms and phrases used in the specification, examples, and appended claims, are provided below. Unless stated otherwise, or implicit from context, the following terms and phrases include the meanings provided below. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs. If there is an apparent discrepancy between the usage of a term in the art and its definition provided herein, the definition provided within the specification shall prevail.

For convenience, certain terms employed herein, in the specification, examples and appended claims are collected here.

The terms "decrease", "reduced", "reduction", or "inhibit" are all used herein to mean a decrease by a statistically significant amount. In some embodiments, "reduce," "reduction" or "decrease" or "inhibit" typically means a decrease by at least 10% as compared to a reference level (e.g. the absence of a given treatment) and can include, for example, a decrease by at least about 10%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, at least about 98%, at least about 99%, or more. As used herein, "reduction" or "inhibition" does not encompass a complete inhibition or reduction as compared to a reference level. "Complete inhibition" is a 100% inhibition as compared to a reference level. A decrease can be preferably down to a level accepted as within the range of normal for an individual without a given disorder.

The terms "increased", "increase", "enhance", or "activate" are all used herein to mean an increase by a staticaly significant amount. In some embodiments, the terms "increased", "increase", "enhance", or "activate" can mean an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level. In the context of a marker or symptom, a "increase" is a statistically significant increase in such level.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, canine species, e.g., dog, fox, wolf, avian species, e.g., chicken, emu, ostrich, and fish, e.g., trout, catfish and salmon. In some embodiments, the subject is a mammal, e.g., a primate, e.g., a human. The terms, "individual," "patient" and "subject" are used interchangeably herein.

Preferably, the subject is a mammal. The mammal can be a human, non-human primate, mouse, rat, dog, cat, horse, or cow, but is not limited to these examples. Mammals other than humans can be advantageously used as subjects that represent animal models of hypertension. A subject can be male or female.

A subject can be one who has been previously diagnosed with or identified as suffering from or having a condition in need of treatment (e.g. hypertension) or one or more complications related to such a condition, and optionally, have already undergone treatment for hypertension or the one or more complications related to hypertension. Alternatively, a subject can also be one who has not been previously diagnosed as having hypertension or one or more complications related to hypertension. For example, a subject can be one who exhibits one or more risk factors for hypertension or one or more complications related to hypertension or a subject who does not exhibit risk factors.

A "subject in need" of treatment for a particular condition can be a subject having that condition, diagnosed as having that condition, or at risk of developing that condition.

As used herein, the terms "protein" and "polypeptide" are used interchangeably herein to designate a series of amino acid residues, connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

As used herein, the term "nucleic acid" or "nucleic acid sequence" refers to any molecule, preferably a polymeric molecule, incorporating units of ribonucleic acid, deoxyribonucleic acid or an analog thereof. The nucleic acid can be either single-stranded or double-stranded. A single-stranded nucleic acid can be one nucleic acid strand of a denatured double-stranded DNA. Alternatively, it can be a single-stranded nucleic acid not derived from any double-stranded DNA. In one aspect, the nucleic acid can be DNA. In another aspect, the nucleic acid can be RNA. Suitable nucleic acid molecules are DNA, including genomic DNA or cDNA. Other suitable nucleic acid molecules are RNA, including mRNA.

As used herein, the terms "treat," "treatment," "treating," or "amelioration" refer to therapeutic treatments, wherein the object is to reverse, alleviate, ameliorate, inhibit, slow down or stop the progression or severity of a condition associated with a disease or disorder, e.g. hypertension. The term "treating" includes reducing or alleviating at least one adverse effect or symptom of a condition, disease or disorder associated with hypertension. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. The term "treatment" of a disease also includes providing relief from the symptoms or side-effects of the disease (including palliative treatment).

As used herein, the term "pharmaceutical composition" refers to the active agent in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject.

The term "statistically significant" or "significantly" refers to statistical significance and generally means a two standard deviation (2SD) or greater difference.

Other than in the operating examples, or where otherwise indicated, all numbers expressing quantities of ingredients or reaction conditions used herein should be understood as modified in all instances by the term "about." The term "about" when used in connection with percentages can mean±1%.

As used herein the term "comprising" or "comprises" is used in reference to compositions, methods, and respective component(s) thereof, that are essential to the method or composition, yet open to the inclusion of unspecified elements, whether essential or not.

The term "consisting of" refers to compositions, methods, and respective components thereof as described herein, which are exclusive of any element not recited in that description of the embodiment.

As used herein the term "consisting essentially of" refers to those elements required for a given embodiment. The term permits the presence of elements that do not materially affect the basic and novel or functional characteristic(s) of that embodiment.

The singular terms "a," "an," and "the" include plural referents unless context clearly indicates otherwise. Similarly, the word "or" is intended to include "and" unless the context clearly indicates otherwise. Although methods and materials similar or equivalent to those described herein can be used in the practice or testing of this disclosure, suitable methods and materials are described below. The abbreviation, "e.g." is derived from the Latin exempli gratia, and is used herein to indicate a non-limiting example. Thus, the abbreviation "e.g." is synonymous with the term "for example."

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); or Methods in Enzymology: Guide to Molecular Cloning Techniques Vol. 152, S. L. Berger and A. R. Kimmel Eds., Academic Press Inc., San Diego, USA (1987); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Other terms are defined herein within the description of the various aspects of the invention.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology described herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are described herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments described herein can be combined to provide further embodiments. Aspects of the disclosure can be modified, if necessary, to employ the compositions, functions and concepts of the above references and application to provide yet further embodiments of the disclosure. Moreover, due to biological functional equivalency considerations, some changes can be made in protein structure without affecting the biological or chemical action in kind or amount. These and other changes can be made to the disclosure in light of the detailed description. All such modifications are intended to be included within the scope of the appended claims.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The technology described herein is further illustrated by the following examples which in no way should be construed as being further limiting.

Some embodiments of the technology described herein can be defined according to any of the following numbered paragraphs:

1. A method of treating hypertension in a subject in need thereof, the method comprising:
    administering an agent that reduces the level of oxidant-modified ET-B Cys405, Cys403, or Cys402.
2. The method of paragraph 1, wherein the subject is in need of treatment for a condition selected from the group consisting of:
    systemic hypertension and pulmonary arterial hypertension.
3. The method of any of paragraphs 1-2, wherein the agent is an ET-B polypeptide comprising an oxidant-resistant mutation at Cys405, Cys403, or Cys402.
4. The method of any of paragraphs 1-3, wherein the agent is a nucleic acid encoding an ET-B polypeptide comprising an oxidant-resistant mutation at Cys405, Cys403, or Cys402.
5. The method of any of paragraphs 1-4, wherein the oxidant-resistant mutation is the substitution of a cysteine with an alanine, valine, leucine, or isoleucine.
6. The method of any of paragraphs 1-5, wherein the oxidant-resistant mutation at Cys405 is selected from: Cys405Ala; Cys405Val; Cys405Leu; and Cys405Ile.
7. The method of any of paragraphs 1-6, wherein the oxidant modification of ET-B Cys405, Cys403, or Cys402 comprises a disulfide bond or the formation of sulfenic acid.
8. A method of potentiating or increasing nitric oxide vasodilatory signaling activity, the method comprising:
    administering an agent that reduces the level of oxidant-modified ET-B Cys405, Cys403, or Cys402.
9. The method of paragraph 8, wherein the agent is an ET-B polypeptide comprising an oxidant-resistant mutation at Cys405, Cys403, or Cys402.
10. The method of any of paragraphs 8-9, wherein the agent is a nucleic acid encoding an ET-B polypeptide comprising an oxidant-resistant mutation at Cys405, Cys403, or Cys402.
11. The method of any of paragraphs 8-10, wherein the oxidant-resistant mutation is the substitution of a cysteine with an alanine, valine, leucine, or isoleucine.
12. The method of any of paragraphs 8-11, wherein the oxidant-resistant mutation at Cys405 is selected from: Cys405Ala; Cys405Val; Cys405Leu; and Cys405Ile.
13. The method of any of paragraphs 8-12, wherein the oxidant modification of ET-B Cys405, Cys403, or Cys402 comprises a disulfide bond or the formation of sulfenic acid.
14. A method of identifying an agent that reduces the level of oxidant-modified ET-B Cys405, Cys403, or Cys402, the method comprising:
    contacting a cell expressing ET-B with a candidate agent and an oxidant; measuring the level of oxidant-modification of ET-B Cys405, Cys403, or Cys402;
    wherein a lower level of oxidant-modification in the presence of the candidate agent indicates the agent is an agent that reduces the level of oxidant-modified ET-B Cys405, Cys403, or Cys402.
15. The method of paragraph 14, wherein the oxidant modification of ET-B Cys405, Cys403, or Cys402 comprises a disulfide bond or the formation of sulfenic acid.

EXAMPLES

Example 1

Aldosterone Inactivates the Endothelin-B Receptor via a Cysteinyl Thiol Redox Switch to Decrease Pulmonary Endothelial Nitric Oxide Levels and Modulate Pulmonary Arterial Hypertension Pulmonary arterial hypertension (PAH) is characterized, in part, by decreased endothelial nitric oxide (NO.) production and elevated levels of endothelin-1. Endothelin-1 is known to stimulate endothelial nitric oxide synthase (eNOS) via the endothelin-B receptor ($ET_B$). Endothelin-1 also stimulates adrenal aldosterone synthesis; in systemic blood vessels, hyperaldosteronism induces vascular dysfunction by increasing endothelial reactive oxygen species (ROS) generation and decreasing NO. levels. The inventors hypothesized that aldosterone modulates PAH by disrupting $ET_B$-eNOS signaling through a mechanism involving increased pulmonary endothelial oxidant stress.

As demonstrated herein, in rats with PAH, elevated endothelin-1 levels were associated with elevated aldosterone levels in plasma and lung tissue and decreased lung NO. metabolites in the absence of left heart failure. Also demonstrated herein, in human pulmonary artery endothelial cells (HPAECs), endothelin-1 increased aldosterone levels via PGC-1α/steroidogenesis factor-1-dependent upregulation of aldosterone synthase. Aldosterone also increased ROS production, which oxidatively modified cysteinyl thiols in the eNOS-activating region of $ET_B$ to decrease endothelin-1-stimulated eNOS activity. Substitution of $ET_B$-Cys405 with alanine improved $ET_B$-dependent NO. synthesis under conditions of oxidant stress, confirming that Cys405 is a redox sensitive thiol that is necessary for $ET_B$-eNOS signaling. In HPAECs, mineralocorticoid receptor antagonism with spironolactone decreased aldosterone-mediated ROS generation and restored $ET_B$-dependent NO. production. Spironolactone or eplerenone prevented or reversed pulmonary vascular remodeling and improved cardiopulmonary hemodynamics in two animal modes of PAH in vivo.

The data described herein demonstrate that aldosterone modulates an $ET_B$ cysteinyl thiol redox switch to decrease pulmonary endothelium-derived NO. and promote PAH.

Pulmonary endothelial reactive oxygen species (ROS) have been implicated in the pathobiology of pulmonary arterial hypertension (PAH) and have been shown to disrupt nitric oxide (NO.)-dependent vasodilatory signaling pathways to promote pulmonary vasoconstriction, muscularization of pulmonary arterioles, and perivascular fibrosis.[1,2] However, contemporary PAH pharmacotherapies that aim to restore pulmonary vascular NO. levels have waning long-term efficacy and do not maintain normal pulmonary vascular tone and pulmonary hemodynamics.[3] This observation suggests that in PAH, perturbations to the redox milieu of pulmonary vascular tissue is sufficient to offset the vasodilatory effects of NO., although the factor(s) that modulate this effect have not been fully elucidated.

Elevated levels of the mineralocorticoid hormone aldosterone are associated with a vasculopathy in systemic blood vessels that is characterized by mineralocorticoid receptor-dependent increases in endothelial ROS generation that decreases levels of bioavailable NO. resulting in vascular endothelial dysfunction, vascular fibrosis, and decreased vascular compliance.[4] In patients with hyperaldosteronism and hypertension or congestive heart failure, mineralocorticoid receptor antagonism with spironolactone or eplerenone improves vascular reactivity and attenuates the adverse effects of aldosterone on blood vessel function and architecture.[5] The inventors hypothesized that hyperaldosteronism is present in PAH owing to increased circulating levels of endothelin-1 (ET-1), which is a potent stimulus of adrenal aldosterone synthesis,[6] and/or overactivation of the renin-angiotensin-aldosterone axis. Together, these observations and the hypothesis described above suggest the possibility that by increasing pulmonary endothelial ROS levels, hyperaldosteronism is an unrecognized contributor to the pathobiology of PAH.

The mechanism(s) by which ROS decreases pulmonary endothelial NO. levels in PAH is unresolved. In the systemic vasculature, ROS has been implicated in the oxidative modification of redox-sensitive cysteinyl thiols in regulatory proteins involved in NO.-dependent vasodilatory signaling to decrease NO. bioactivity.[7] A key source of endogenous NO. generation in pulmonary endothelial cells is via endothelin type B receptor ($ET_B$)-mediated activation of endothelial nitric oxide synthase (eNOS).[8] $ET_B$ contains an intracellular cysteine-rich region near its carboxyterminal domain that includes Cys405, a cysteinyl thiol[9]. Taken together, the inventors hypothesized that oxidative modification of $ET_B$ Cys405 by aldosterone-induced ROS serves as a redox switch that disables $ET_B$-dependent synthesis of NO. to promote pulmonary vascular dysfunction and negative remodeling of pulmonary arterioles in PAH.

Methods

Cell culture and treatments. Human pulmonary artery endothelial cells (HPAECs) (Lonza) (male donors) were grown to confluence using phenol-free EGM-2 medium supplemented with 5% fetal bovine serum at 37° C., 5% $CO_2$. Cells were passaged twice-weekly using 0.5% trypsin/EDTA, and experiments were performed on cells from passages 4-10. Aldosterone (Steraloids) and ET-1 (1-100 nM) (Sigma-Aldrich) were dissolved in dimethylsufloxide (10 nmol/L) and deoxygenated water, respectively, which served as vehicle controls. Cells were treated with aldosterone ($10^-$–$10^{-7}$ mol/L) for 24 h and in selected experiments co-incubated with the mineralocorticoid receptor inhibitor spironolactone (10 µM/l) (Sigma-Aldrich).

Western analysis to detect $ET_B$ disulfide bond formation. Western analysis to detect $ET_B$ disulfide bond formation was performed as described previously.[7] Briefly, protein extracts from cells were lysed in alkylating buffer containing 0.1 M Tris-HCL, pH 6.8, 1% SDS, 100 mM iodoacetamide, and 100 mM N-ethylmaleimide, and sonicated on ice for 5 min followed by a 30-min incubation at 25° C. Alkylated proteins were then precipitated with acetone. Proteins were resuspended in 50 µl of 0.1 M Tris-HCl, pH 7.4, 1% SDS; and disulfides were reduced with 5 mM tris(2-carboxyethyl) phosphine hydrochloride (TCEP). Following a 20-min incubation at 25° C., TCEP was removed with a Micro Bio-Spin™ column 6 (Bio-Rad), and 1% SDS was added to the eluant. The cysteines previously participating in a disulfide bond, now reduced, were labeled with 1 mM polyethylene glycol-conjugated maleimide (molecular mass 10 kDa) (Fluka). After a 1-h incubation at 25° C., proteins were precipitated with acetone, resuspended in 50 µl of non-reducing SDS electrophoresis buffer, and boiled for 10 min. Protein samples were then size-fractionated electrophoretically using SDS-PAGE, and transferred to a polyvinylidene fluoride membrane. The membrane was immunoblotted with an anti-$ET_B$ antibody to the region of $ET_B$ that contains Cys405 (amino acid sequence to which $ET_B$ antibody was raised: clccwcqsfeekqsleekqsclkfkandhgydnfrssnkysss (SEQ ID NO: 1)) (Santa Cruz Biotechnology). Bands were visualized using the ECL detection method.[4]

Animal model of PAH. Male Sprague-Dawley rats (age 12-14 weeks; Charles River Laboratories) were handled in accordance with US National Institutes of Health guidelines, and all procedures were approved by the local committee at Brigham and Women's Hospital, Harvard Medical School. All surgeries were performed under ketamine/xylazine anesthesia. For the monocrotaline (MCT) model of PAH, rats were fed standard chow and treated with a 0.5 ml intraperitoneal injection of MCT (50 mg/ml) (Sigma-Aldrich) or 0.9% saline as control. Rats were randomized to spironolactone (25 mg/kg/d) (Henry Schein) or vehicle added to the drinking water. For the prevention study, treatment with spironolactone began immediately following administration of MCT and continued for 23-25 days until hemodynamic and tissue analyses were performed. For the reversal study, a second experiment was performed in which rats were randomized to spironolactone or vehicle that was initiated 14 days following the administration of MCT and continued until hemodynamic and tissue analyses were performed 10 days later.

For SU-5416/hypoxia-induced PAH, rats (~225 g) were administered a single subcutaneous injection of the vascular endothelial growth factor (VEGF)-2 inhibitor SU-5416 (20 mg/kg; Sigma) and exposed immediately to chronic hypoxia (barometric pressure, 410 mm Hg; inspired $O_2$ tension 76 mm Hg) as described previously.[10] Rats were randomized to either the selective mineralocorticoid receptor antagonist eplerenone (0.6 mg/1 gm standard chow; Test Diet Inc.) or standard chow as a control.[11] Hemodynamic and tissue analyses were performed on all rats 21 days following exposure to chronic hypoxia.

Statistical analysis. Continuous data are expressed as mean±S.E.M. Comparison between groups was performed by Student's paired two-tailed t-test. One-way analysis of variance (ANOVA) was used to examine differences in response to treatments between groups, with post-hoc analysis performed by the method of Tukey. P<0.05 was considered significant.

Results

PAH is associated with increased plasma and lung tissue levels of ET-1 and aldosterone. The Sprague Dawley rat monocrotaline (MCT) model of PAH was selected initially to test the hypothesis that hyperaldosteronism is present in PAH in vivo as MCT is believed to induce pulmonary hypertension through a mechanism that involves elevated levels of the aldosterone secretagogue ET-1.[12] Transthoracic echocardiography demonstrated that compared to vehicle control (V)-treated rats, MCT decreased the pulmonary artery (PA) flow acceleration time (PAAT) (35.4±2.6 vs. 14.1±1.2 msec, p<0.001, n=6) and increased right ventricular (RV) free-wall thickness (0.58±0.05 vs. 1.1±0.05 mm, p<0.001, n=6). Right heart catheterization confirmed that MCT increased significantly pulmonary artery systolic pressure (PASP) (assumed to be equivalent to RV systolic pressure in the setting of a normal pulmonic valve) (28.3±2.7 vs. 89.3±5.3 mm Hg, p<0.001, n=6). In rats with PAH, there was a 286% increase in ET-1 levels in plasma (p<0.04, n=6) and a 174% increase in lung homogenates (p<0.04, n=4) (FIGS. 1A-1B), which correlated with an increase in aldosterone levels of 406% (p<0.001, n=4) and 172% (p<0.001, n=4) in plasma and lung tissue, respectively (FIGS. 1C-1D).

Figure 9:
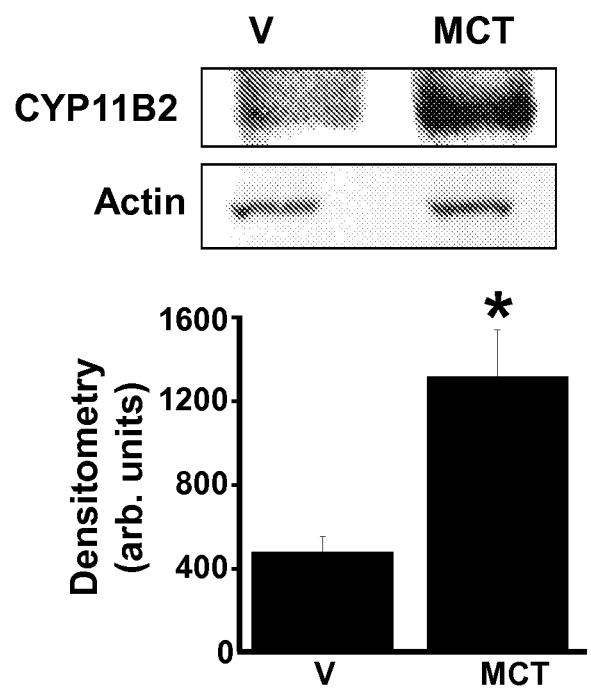
FIG. 9 depicts western blot results and the quantification thereof, demonstrating that PAH is associated with increased lung tissue CYP11B2 protein levels. Lung tissue was isolated from male Sprague-Dawley rats treated with vehicle control (V) or monocrotaline (MCT) (50 mg/kg) for 25 days to induce PAH and CYP11B2 (aldosterone synthase) expression was examined in homogenates by Western analysis. *p<0.03 vs. V, n=4. Arb. units, arbitrary units. Data are expressed as mean±S.E.M. Representative blots are shown.

The finding of increased aldosterone levels in lung tissue suggested that PAH may be associated with extraadrenal aldosterone synthesis. To determine if this occurred, lungs were examined for expression of the enzyme CYP11B2 (aldosterone synthase), which catalyzes the final and rate-limiting step in aldosterone steroidogenesis. Following saline perfusion of lungs prior to organ harvest, protein levels of CYP11B2 were increased significantly in lung tissue of rats with PAH compared to controls (483±75 vs. 1319±226 arb. units, p<0.05, n=4) (FIG. 9), indicating that it is plausible that elevated levels of aldosterone in lung tissue may also result from local synthesis of aldosterone in PAH.

Figures 2A, 2B, 2C:
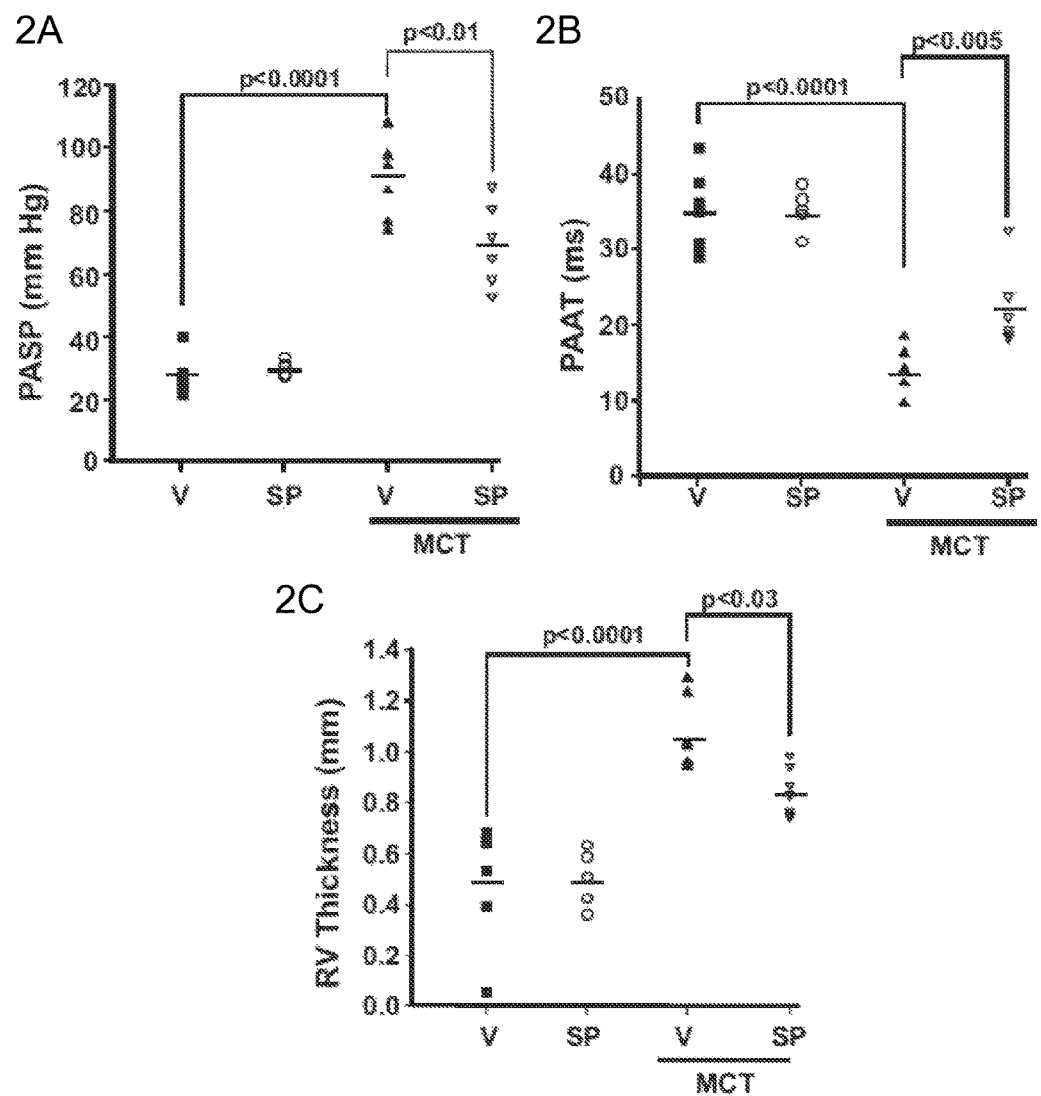
FIGS. 2A-2C depict graphs demonstrating that aldosterone promotes PAH in vivo. Sprague-Dawley rats were treated with vehicle control (V) or monocrotaline (MCT) (50 mg/kg) and randomized immediately to V or spironolactone (SP) (25 mg/kg/d) for 25 days. The contribution of aldosterone to PAH was assessed by (FIG. 2A) right heart catheterization to measure pulmonary artery (assumed to be equivalent to right ventricular) systolic pressure (PASP); echocardiography to assess changes in (FIG. 2B) pulmonary artery acceleration time (PAAT); and, (FIG. 2C) right ventricular (RV) free-wall thickness. *$p<0.001$ vs. V; **$p<0.05$ vs. MCT, n=6 rats per condition. Data are expressed as mean±S.E.M.
Figures 3A, 3B, 3C:
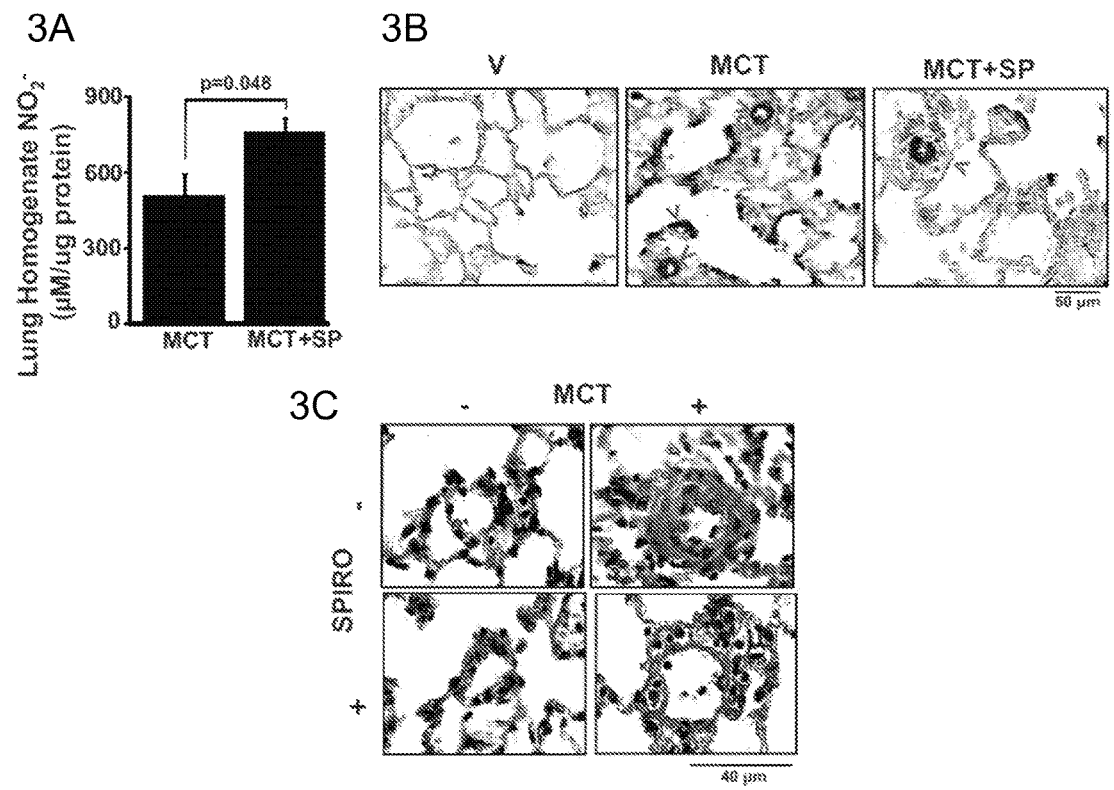
FIGS. 3A-3C depict a graph and immunohistochemistry images demonstrating that spironolactone increases pulmonary vascular NO. levels and attenuates pulmonary vascular remodeling in PAH.
Figure 10A:
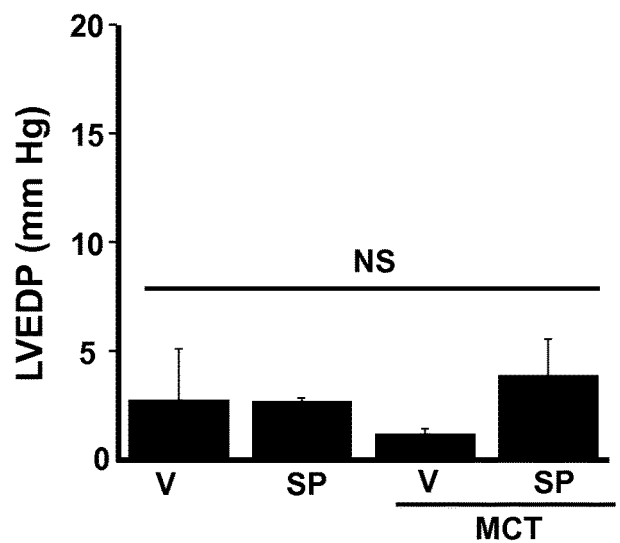
FIGS. 10A-10B depict graphs demonstrating that aldosterone does not affect systemic blood pressure or left ventricular hemodynamics in PAH. Male Sprague-Dawley rats were treated with vehicle control (V) or monocrotaline (MCT) (50 mg/kg) and randomized immediately to V or spironolactone (25 mg/kg/d) in the drinking water. Following treatment for 25 days, the contribution of aldosterone to changes in (FIG. 10A) central aortic mean arterial pressure (MAP) and (FIG. 10B) left ventricular end-diastolic pressure (LVEDP) were assessed by cardiac catheterization. SP, spironolactone. Data are expressed as mean±S.E.M.
Figure 10B:
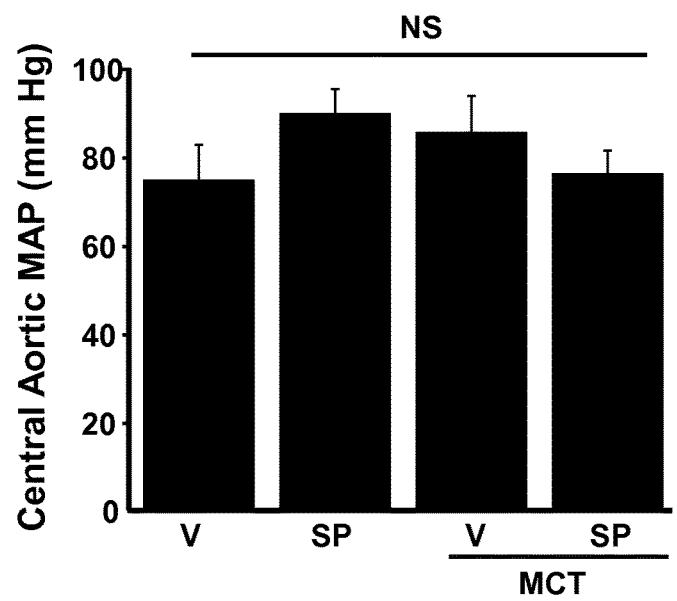
Figures 11, 12:
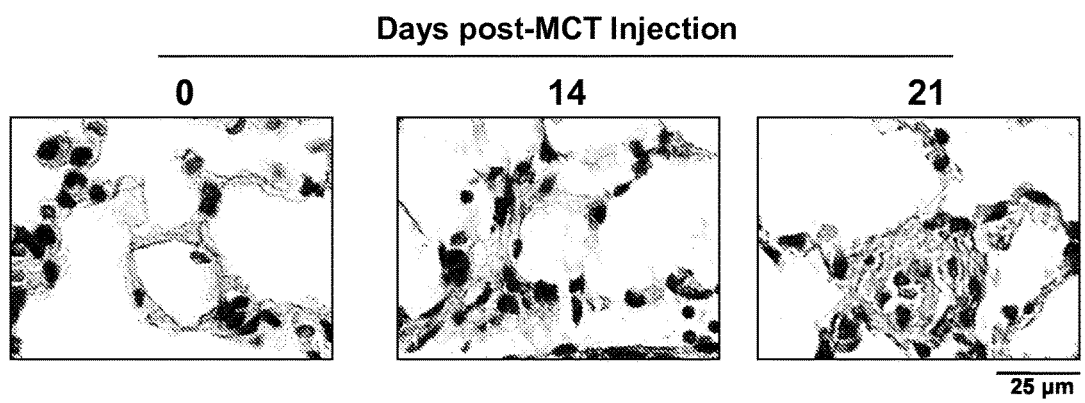
FIG. 11 depicts a table demonstrating that spironolactone decreases right ventricular weight in PAH. Hearts from rats with and without monocrotaline (MCT)-induced PAH and treatment with vehicle control or spironolactone (25 mg/kg/d) for 25 days were dissected immediately after sacrifice. The weights of the right ventricle (RV) and left ventricle (LV), which included the interventricular septum, were recorded. *p<0.05 vs. vehicle control, n=4-5 rats. MCT, monocrotaline; SP, spironolactone. Data are presented as mean±S.E.M.
FIG. 12 depicts immunochemistry images demonstrating that pulmonary vascular injury is evident at 14 days following administration of monocrotaline. Perivascular inflammatory cell infiltrate was assessed by hematoxylin and eosin staining of distal pulmonary arterioles harvested from Sprague-Dawley rats 0, 7, and 14 days following injection of monocrotaline (MCT)(50 mg/kg) (n=3 rats per time point). Representative photomicrographs shown (400× magnification).

Aldosterone increases pulmonary artery pressure and pulmonary vascular remodeling in PAH in vivo. To determine if hyperaldosteronism contributes to increased pulmonary artery pressure in PAH in vivo and if mineralocorticoid receptor antagonism could prevent PAH, rats were treated with spironolactone (25 mg/kg/d) or V starting at the time of MCT injection. It was observed that without significantly decreasing plasma ET-1 levels or influencing body weight, mean arterial pressure (MAP), or left ventricular end-diastolic pressure (LVEDP) (FIGS. 10A-10B), spironolactone decreased PASP significantly in PAH (89.3±5.2 vs. 69.5±5.4 mm Hg, p<0.04, n=6) (FIG. 2A), which was confirmed by an increase in PAAT (14.1±1.2 vs. 22.3±2.2 ms, p<0.05, n=6) (FIG. 2B). Spironolactone also decreased RV free-wall thickness (1.07±0.05 vs. 0.86±0.03 mm, p<0.05, n=6) (FIG. 2C) and RV weight (0.43±0.07 vs. 0.35±0.04 RV weight/LV septum weight, p=0.32, n=5) (FIG. 11). Notably, these findings were associated with increased levels of the stable NO. metabolite, nitrite ($NO_2^-$), in lung tissue specimens harvested from spironolactone-treated rats with PAH as compared to V-treated rats with PAH (759±55 vs. 506±86 μM/μg protein, p=0.05, n=4) indicating that spironolactone improved NO. bioavailability (FIG. 3A).

Spironolactone also prevented pathophenotypic changes to distal pulmonary arterioles [located distal to terminal bronchioles with diameters 20-50 μm[13]] as demonstrated by immunohistochemical staining for smooth muscle α-actin. Compared to V-treated rats with PAH, spironolactone decreased the number of α-actin-stained muscularized distal pulmonary arterioles (77.7±6.3 vs. 59.7±0.4 muscularized pulmonary arterioles/20 high powered fields, p<0.05, n=5) (FIG. 3B), and increased significantly the cross-sectional luminal area of vessels (14.3±0.7 vs. 35.4±1.9% cross sectional area, p<0.05, n=5). Furthermore, Gomori's trichrome staining of rat lung sections revealed that, compared to V-treated rats with PAH, spironolactone decreased perivascular collagen deposition by 77% (p<0.05, n=4), similar to levels observed in rats without PAH (FIG. 3C). Analysis using picrosirius red staining paralleled these findings, indicating that hyperaldosteronism contributed to perivascular collagen deposition (i.e., fibrillar collagen), which, in turn, is strongly associated with impaired vascular compliance in PAH.[1] Paraffin-embedded lung sections obtained from rats with and without monocrotaline (MCT)-induced PAH and treated with vehicle control or spironolactone (25 mg/kg/d) for 25 days were stained with picrosirius red and analyzed by polarized light microscopy. Levels of fibrillar collagen were assessed in the wall of pulmonary arterioles measuring 20-50 μM and located distal to terminal bronchioles (data not shown).

Figures 4A, 4B:
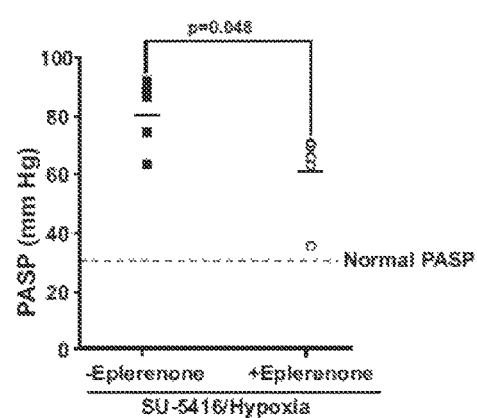
FIGS. 4A-4B depict a table and graph of the effect of mineralocorticoid receptor antagonism on reversal or prevention of adverse cardiopulmonary hemodynamics in two models of experimental PAH.

To determine if aldosterone antagonism reverses established PAH, a second study was performed in which V or spironolactone (25 mg/kg/d) was initiated 14 days following administration of MCT, a time point associated with histological evidence of MCT-induced inflammatory injury to distal pulmonary arterioles (FIG. 12). Compared to V-treated rats with PAH, spironolactone decreased levels of perivascular collagen by 71% (n=6, p<0.003), which was associated with a significant decrease in indexed pulmonary vascular resistance (PVRi) (35.9±3.2 vs. 21.5±3.2 mm Hg*min*g/ml, n=4, p<0.05) and PASP (60.3±5.2 vs. 39.5±4.1 mm Hg, n=6, p<0.05) without changes to heart rate, cardiac index (CI), LVEDP, MAP, or indexed systemic vascular resistance (SVRi) (FIG. 4A).

Next, to confirm the role of aldosterone in a second animal model of PAH and to determine if there was a class effect for mineralocorticoid receptor antagonists, the preventive effects of eplerenone on the development of abnormal cardiopulmonary hemodynamics in rats administered SU-5416 and exposed to chronic hypoxia for 21 days was determined. Compared to normal rats, plasma aldosterone levels were increased by 418% in SU-5416/hypoxia-induced PAH (n=5, p<0.05). Eplerenone decreased perivascular collagen in SU-5416/hypoxia-induced PAH by 67% (n=5, p<0.05), which was associated with a significant decrease in PVRi (64.6±21.4 vs. 43.9±8.7 mm Hg*min*gm/ml, n=3-4 rats/condition, p=0.18) and PASP (80.5±4.9 vs. 61.5±6.5 mm Hg, p=0.048, n=5) (FIG. 4B) without significantly influencing body weight, heart rate, MAP, CI, LVEDP, or SVRi. Collectively, these findings demonstrate that hyperaldosteronism modulates PAH and that a class effect exists among mineralocorticoid receptor antagonists for abrogating the adverse consequences of aldosterone on pulmonary vascular remodeling, PVRi, and PASP in two animal models of PAH in vivo.

ET-1 increases aldosterone levels in pulmonary artery endothelial cells. As ET-1 levels associated positively with lung CYP11B2 protein expression and aldosterone levels in MCT-induced PAH in vivo, the possibility that ET-1 is an unrecognized stimulus of extraadrenal aldosterone synthesis in HPAECs in vitro was explored. It was first confirmed that compared to V-treated cells, ET-1 (1, 10, 100 nM) increased CYP11B2 protein expression levels (157.3±27.5 vs.

Figure 14:
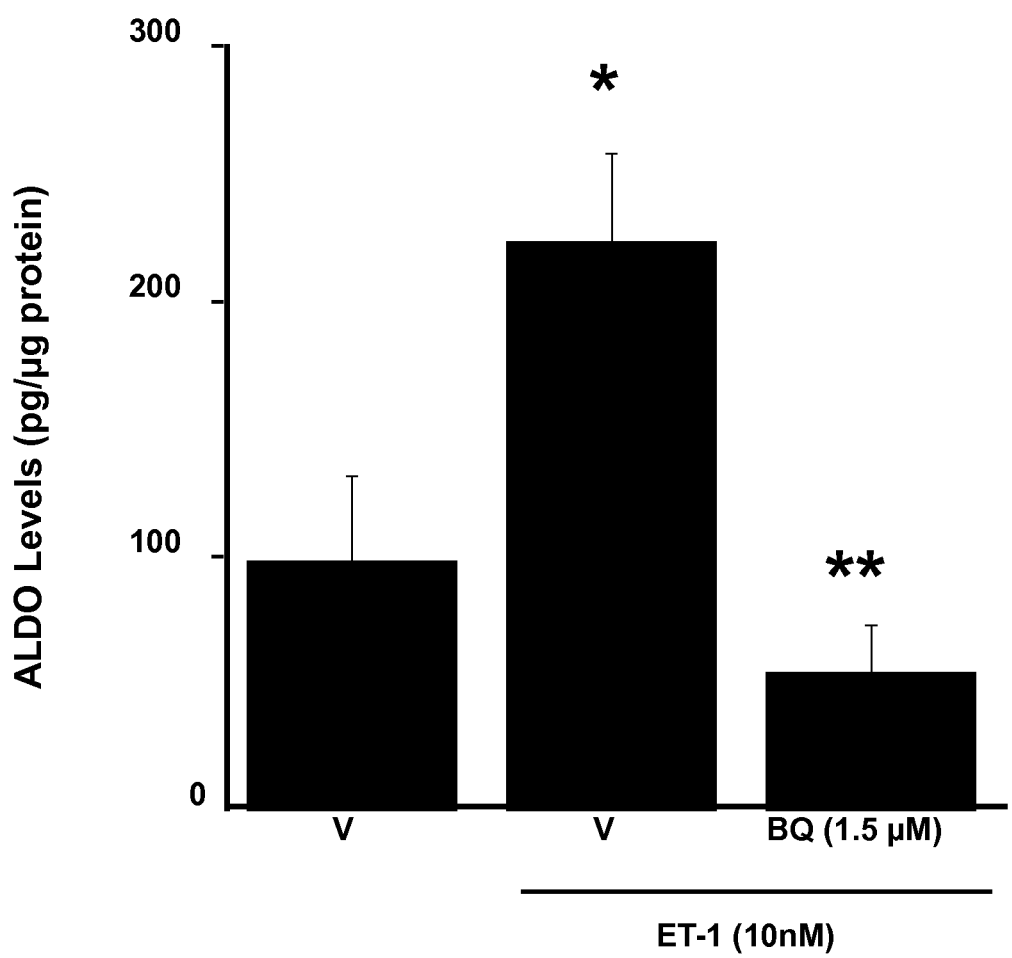
FIG. 14 depicts a graph demonstrating that ET-1 increases aldosterone in an $ET_B$-dependent manner. HPAECs were exposed to vehicle control (V) or ET-1 (10 nM) for 24 h in the presence or absence of the selective $ET_B$ antagonist BQ-788 (1.5 µM), and aldosterone (ALDO) levels were measured in the culture medium. *p<0.05 vs. V, **p<0.05 vs. ET-1, n=4. Data are presented as mean±S.E.M.

180.4±13.4 vs. 234.8±4.3% control, respectively, p<0.05, n=3) (FIG. 13A), which correlated with a concentration-dependent increase in aldosterone levels detected in the cell culture medium (241.1±44.8 vs. 283.5±94.7 vs. 396.0±116.5% control, respectively, p<0.05, n=4) (FIG. 13B). Consistent with prior reports in dispersed adrenal cortical cells,[6,14] ET-1 increased aldosterone levels via activation of the $ET_B$ receptor in HPAECs (FIG. 14).

Figure 5A:
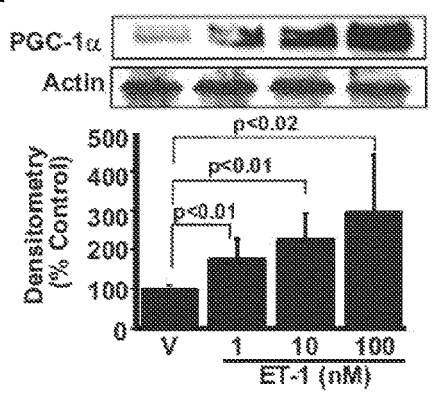
FIGS. 5A-5D depict immunochemistry results and graphs demonstrating that ET-1 stimulates PGC-1α-dependent association of SF with CYP11B2 to increase aldosterone levels.
Figure 5B:
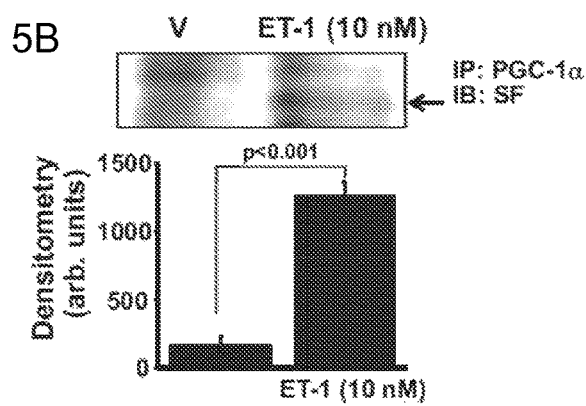

It was next sought to determine the mechanism by which ET-1 increases aldosterone levels in HPAECs. In adrenal cortical Y-1 cells, the transcription factor PPAR-γ co-activator-1α (PGC-1α) interacts with the nuclear receptor protein steroidogenesis factor-1 (SF) to regulate CYP11B2 gene transcription and induce aldosterone synthesis.[15] Therefore, to determine if ET-1 increased aldosterone synthase protein levels by this mechanism in HPAECs, the effect of ET-1 on PGC-1α and SF protein expression levels in these cells was determined. Compared to V-treated cells, exposure to ET-1 (1, 10, 100 nM) for 24 h induced a concentration-dependent increase in PGC-1α a protein expression levels (176.5±52.8 vs. 224.7±68.1 vs. 296.7±145.8% control, respectively, p<0.05, n=3) (FIG. 5A). ET-1 had no effect on SF protein levels; however, ET-1 did increase the association between PGC-1α and SF as demonstrated by co-immunoprecipitation (1260±104 vs. 160±71 arb. units, p<0.03, n=3) (FIG. 5B).

Figure 5C:
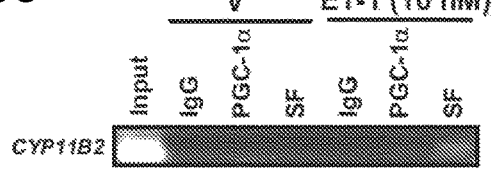
Figure 5D:
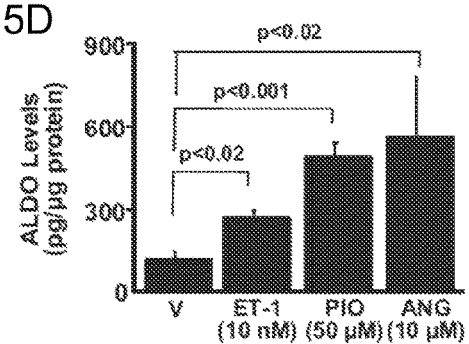

A chromatin immunoprecipitation assay was next performed to assess the effect of ET-1 (10 nM) for 24 h on PGC-1α and/or SF association with the CYP11B2 promoter. PGC-1α alone did not bind to the CYP11B2 promoter in cells treated with either V or ET-1; however, compared to V, ET-1 induced a significant increase in SF binding to the CYP11B2 promoter (16.3±9.8 vs. 61.6±9.3 arb. units, p<0.03, n=3) (FIG. 5C). Collectively, these data indicate that ET-1 stimulates PGC-1α binding with SF, which, in turn, promotes the association of SF to the promoter region of CYP11B2 to upregulate CYP11B2 protein expression levels. It was confirmed that PGC-1α stimulation is linked functionally to aldosterone synthesis in cells treated with the selective PGC-1α agonist pioglitazone (50 μM) for 24 h, which, compared to V, increased aldosterone levels by 365% (p<0.01, n=3) (FIG. 5D). Thus, ET-1 increases extraadrenal aldosterone synthesis in endothelial cells via upregulation of CYP11B2 in a PGC 1-α/SF-dependent manner.

Figure 15A:
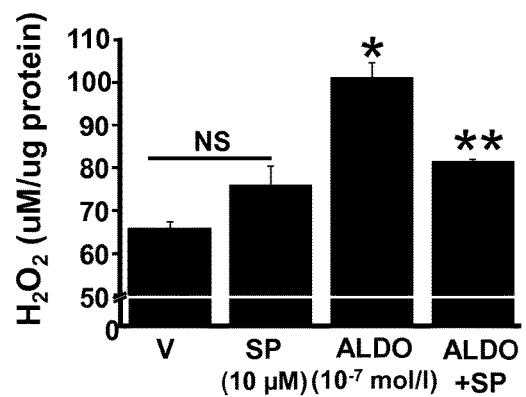
FIGS. 15A-15C depict graphs and immunochemistry results demonstrating that aldosterone increases NOX4 expression to increase oxidant stress in HPAECs.

Aldosterone increases oxidant stress in HPAECs. Next, to determine if hyperaldosteronism in PAH could contribute to pulmonary vascular dysfunction akin to what was observed previously in the systemic vasculature,[4,7] the effect of aldosterone on ROS levels in HPAECs was observed. Cells were exposed to increasing concentrations of aldosterone ($10^{-9}$, $10^{-8}$, $10^{-7}$ mol/L) for 12-36 h and $H_2O_2$ levels were measured by Amplex Red assay. Compared to V-treated cells, maximal $H_2O_2$ accumulation was observed in cells treated with aldosterone ($10^{-7}$ mol/L) for 24 h (65.4±1.6 vs. 100.6±3.5 μM/mg protein, p<0.05, n=3); this effect was abrogated by 56% in aldosterone-treated cells coincubated with spironolactone (p<0.05, n=3), indicating that a majority of aldosterone-induced $H_2O_2$ formation was due to mineralocorticoid receptor activation (FIG. 15A). As no further $H_2O_2$ generation was observed in aldosterone-treated cells beyond 24 h, subsequent experiments were performed at this time point using (patho)physiologically relevant levels of aldosterone similar to those observed in MCT- or SU-5416/hypoxia-treated rats with PAH in vivo. Furthermore, the observed increase in ROS was due to aldosterone, and not ET-1, as ET-1 (10 nM) had no effect on $H_2O_2$ levels compared to V-treated cells (p=0.43, n=4).

Figure 15B:
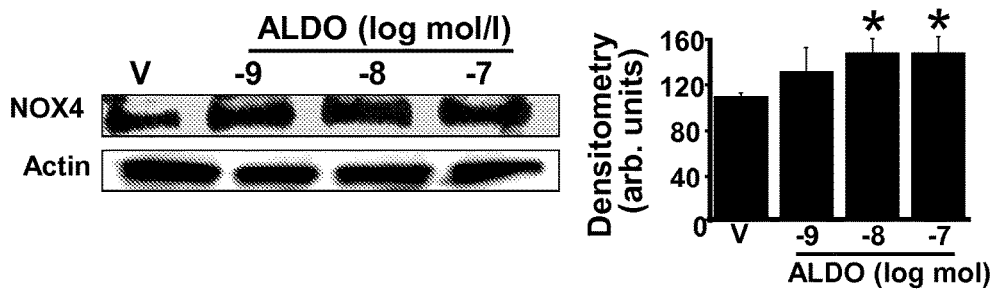
Figure 15C:
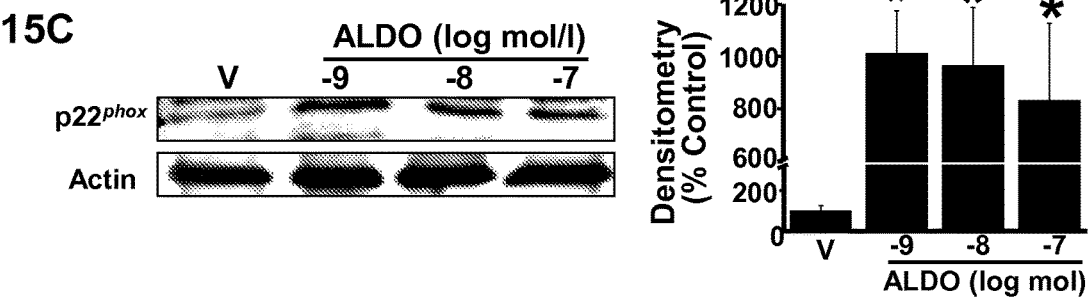

NADPH oxidase type 4 (NOX4) is implicated as a key source of vascular ROS generation in pulmonary hypertension and human vascular endothelial cells exposed to pathophysiologic concentrations of aldosterone.[16,17] The primary product of NOX4 activation is $H_2O_2$, and its formation is closely aligned to changes in NOX4 protein expression.[17] Therefore, the effect of aldosterone on NOX4 expression in HPAECs was examined as a potential mechanism to explain the aldosterone-mediated increase in $H_2O_2$ formation. Compared to V-treated cells, aldosterone ($10^{-9}$, $10^{-8}$, $10^{-7}$ mol/L) increased protein levels of NOX4 (134.6±16.5 vs. 146.3±12.4±vs. 157.0±4.4% control, respectively, p<0.05, n=3) and of $p22^{phox}$ (1009.4±167.0 vs. 961±226.2 vs. 829.5±295.6% control, respectively, p<0.05, n=3), a NOX4 subunit that is required for NOX4-mediated $H_2O_2$ formation, in a concentration-dependent manner (FIGS. 15B-15C).

Figure 16:
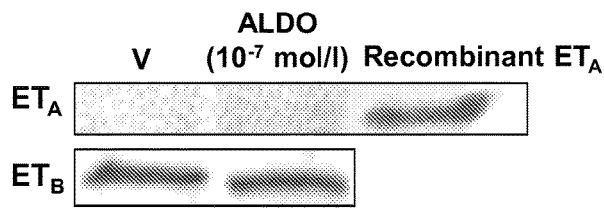
FIG. 16 depicts a western blot demonstrating that aldosterone does not influence $ET_A$ or $ET_B$ protein levels in HPAECs. HPAECs were exposed to vehicle control (V) or aldosterone (ALDO)($10^{-7}$ mol/l) for 24 h and Western analysis (n=3) was performed to monitor for changes in protein expression levels of $ET_A$ and $ET_B$. For $ET_A$ analyses, purified recombinant $ET_A$ receptor protein was used as a positive control. Representative blots are shown.

Aldosterone decreases $ET_B$-dependent activation of eNOS and NO. levels. The effect of $ET_B$ receptor activation by ET-1 (10 nM) on levels of the NO. metabolite nitrite ($NO_2^-$) was next examined. Compared to V-treated cells, ET-1 increased $NO_2^-$ generation with a maximum effect observed at 10 min (29.4±3.6 vs. 139.4±31.8μM/μg protein, p<0.03, n=3). The effect of aldosterone on $ET_B$-stimulated NO. levels was then evaluated. Without influencing protein expression of $ET_B$, or inducing expression of $ET_A$ (which is not constitutively expressed in HPAECs)[18] (FIG. 16), exposure to aldosterone ($10^{-7}$ mol/L) for 24 h decreased $ET_B$-mediated $NO_2^-$ levels by 60.3% (p<0.05, n=3). Coincubation with spironolactone (10 μM) restored $NO_2^-$ levels to those observed in cells stimulated with ET-1 in the absence of aldosterone (FIG. 6A).

Figures 17A, 17B:
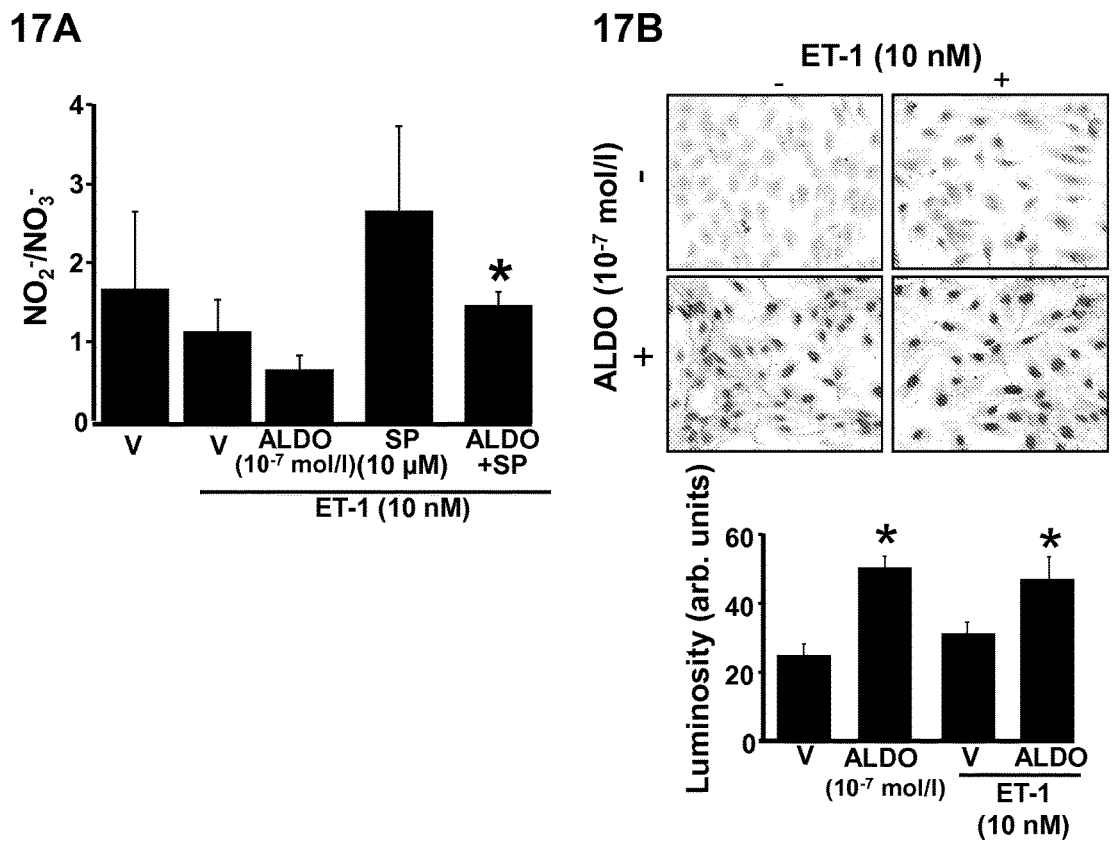
FIGS. 17A-17B depict graphs and immunochemistry images demonstrating that aldosterone increases peroxynitrite formation to decrease $NO_2^-/NO_3^-$.

In the absence of oxidant stress, NO. metabolism to $NO_2^-$ and nitrate ($NO_3^-$) occurs in a ratio that favors $NO_2^-$ by approximately 2:1, but this ratio shifts in favor of increased $NO_3^-$ formation in the presence of superoxide anion ($.O_2^-$), owing to the interaction of $NO_2^-$ with $.O_2^-$ to generate peroxynitrite ($O_2NOO^-$)[7] or via tautomerization of peroxynitrite ($ONOO^-$) to $NO_3^-$.[19] In HPAECs, ET-1 alone did not affect the $NO_2^-/NO_3^-$ ratio significantly compared to V. In contrast, exposure to aldosterone decreased the $NO_2^-/NO_3^-$ ratio by 62% in ET-1-stimulated cells (p<0.04, n=3) (FIG. 17A). This effect was likely mediated by increased $ONOO^-$ formation as aldosterone-treated HPAECs had increased levels of 3-nitrotyrosine, a marker of $ONOO^-$, compared to cells stimulated with V or ET-1 alone (24.1±3.3 vs. 31.2±3.2 vs. 46.8±6.6 arb. units, p<0.05, n=5) (FIG. 17B).

The effect of aldosterone on ET-1-stimulated eNOS activity was also examined. Without influencing eNOS protein levels, aldosterone decreased eNOS activity in ET-1 (10 nM) stimulated cells (18.5±3.5 vs. 7.6±2.4 [$^{14}$C] L-citrulline c.p.m./μg protein, n=3, p<0.05) (FIG. 6B), leading to a decrease in total NO. metabolite (NOx: $NO_2^-+NO_3^-$) formation (157.9±12.7 vs. 103.4±12.2 μM/μg protein, p<0.01, n=3). Coincubation with spironolactone increased NOx levels in aldosterone-treated cells stimulated with ET-1 by 87% (n=3, p<0.05) (FIG. 6C). Taken together, these data demonstrate that aldosterone diminished levels of bioavailable NO. in ET-1-stimulated cells by decreasing ET-1-mediated eNOS activity to limit NO. generation, increasing $ONOO^-$ formation, and by oxidizing $NO_2^-$ to $NO_3^-$.

Aldosterone decreases $ET_B$-dependent NO. levels by oxidative modification of Cys405. Given that aldosterone decreased ET-1-stimulated eNOS activity and NO. generation, the inventors postulated that aldosterone affected $ET_B$ receptor function. As aldosterone induced $H_2O_2$ formation and $ET_B$ contains functionally essential cysteinyl thiol residues in its eNOS-activating region, it was hypothesized that aldosterone can induce an oxidative post-translational modification of $ET_B$ that influences receptor function. To examine $ET_B$ for oxidation of cysteinyl thiols, protein extracts from HPAECs were treated with V, aldosterone ($10^{-7}$ mol/L) for 24 h, or $H_2O_2$ (200 µmol/L) for 20 min, and free thiols were blocked with iodoacetamide and N-ethylmaleimide. Disulfides were reduced with TCEP hydrochloride, and previously oxidized (now reduced) cysteines were labeled with PEG-conjugated maleimide (molecular mass 10 kDa). In this way, each reduced disulfide bond yields a shift in the apparent molecular mass of the reduced protein by 20 kDa. Western analysis using an antibody specific to the region of $ET_B$ containing Cys405 revealed that only the reduced form of $ET_B$ was present (50 kDa) in V-treated cells; however, bands at 70 kDa and 90 kDa were evident in cells treated with $H_2O_2$ or aldosterone, indicating the de novo formation of one or two disulfide bonds under these conditions of increased oxidant stress (FIG. 6D).

To support these findings, it was determined if aldosterone modulates the formation of other higher oxidative intermediates of $ET_B$ Cys405. Cells were treated V or aldosterone ($10^{-7}$ mol/L) for 24 h and the region of $ET_B$ containing Cys405 was immunoprecipitated using the specific $ET_B$ containing Cys405 antibody (Santa Cruz). Western analysis using an anti-sulfenic acid (R—SOH) antibody (derivatized with dimedone)[20] (Millipore) revealed that compared to V-treated cells, aldosterone increased $ET_B$-SOH protein expression levels by 639% (n=3, p<0.05)(FIG. 6E).

Figures 7A, 7B, 7C:
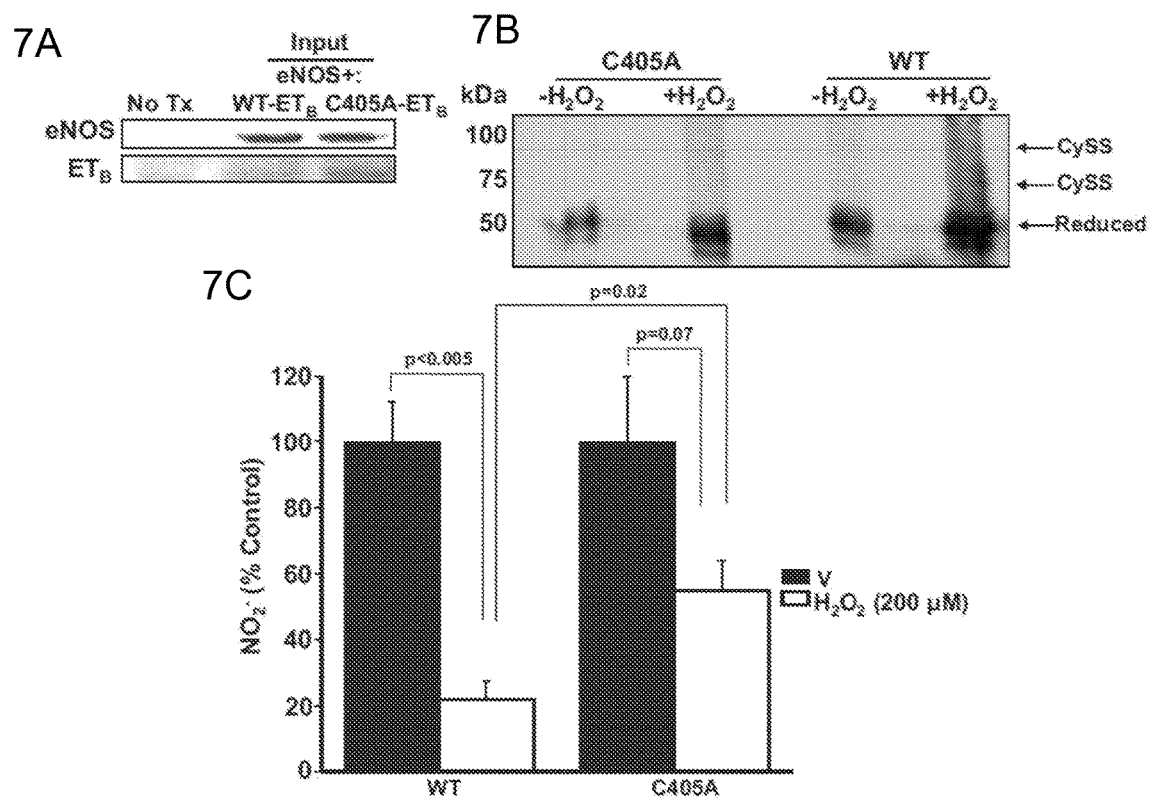
FIGS. 7A-7C depict immunochemistry and graphs demonstrating that oxidation of Cys405 impairs $ET_B$-dependent NO. generation.

To confirm that oxidative modification of Cys405 has functional implications for $ET_B$-dependent NO. generation, COS-7 cells were transiently transfected with human DNAs coding for wild type (WT)-eNOS and WT-$ET_B$ or a mutant $ET_B$ containing a substitution of cysteine with alanine, which is insensitive to oxidant stress, at position 405 (C405A-$ET_B$). Expression of transiently transfected WT-eNOS and WT-$ET_B$ or C405A-$ET_B$ DNA was established by immunoblotting (FIG. 7A). Additionally, immunoblotting of PEG-conjugated maleimide-labeled extracts confirmed that compared to WT-$ET_B$, in which $H_2O_2$ (200 µmol/L for 20 min) induced the formation of one or two disulfide bonds, C405A-$ET_B$ was resistant to the formation of disulfide bonds (FIG. 7B). Next, COS-7 cells expressing eNOS and WT-$ET_B$ or C405A-$ET_B$ were exposed to $H_2O_2$ (200 µmol/L) for 60 min and $ET_B$-dependent NO. synthesis was assessed. This treatment time point was selected because activation of eNOS by $H_2O_2$ is time-dependent and attenuated fully within 60 min following exposure of eNOS to $H_2O_2$.[21] After this time, the medium was replaced and cells were treated with ET-1 (10 nM) for 10 min to stimulate $ET_B$ signal transduction. Although exposure to $H_2O_2$ decreased ET-1-stimulated $NO_2^-$ formation by 78.0% in WT-$ET_B$ transfected cells compared to V-treated cells (p<0.002, n=4), this effect was attenuated significantly in C405A-$ET_B$-transfected cells in which $H_2O_2$ decreased nitrite levels by only 45.0% compared to V-treated cells (p=0.07, n=4) (FIG. 7C). Taken together, these data confirm that Cys405 is a redox sensitive, functional cysteinyl thiol whose oxidation to sulfenic acid impairs $ET_B$-dependent NO. generation.

Discussion

Figure 8:
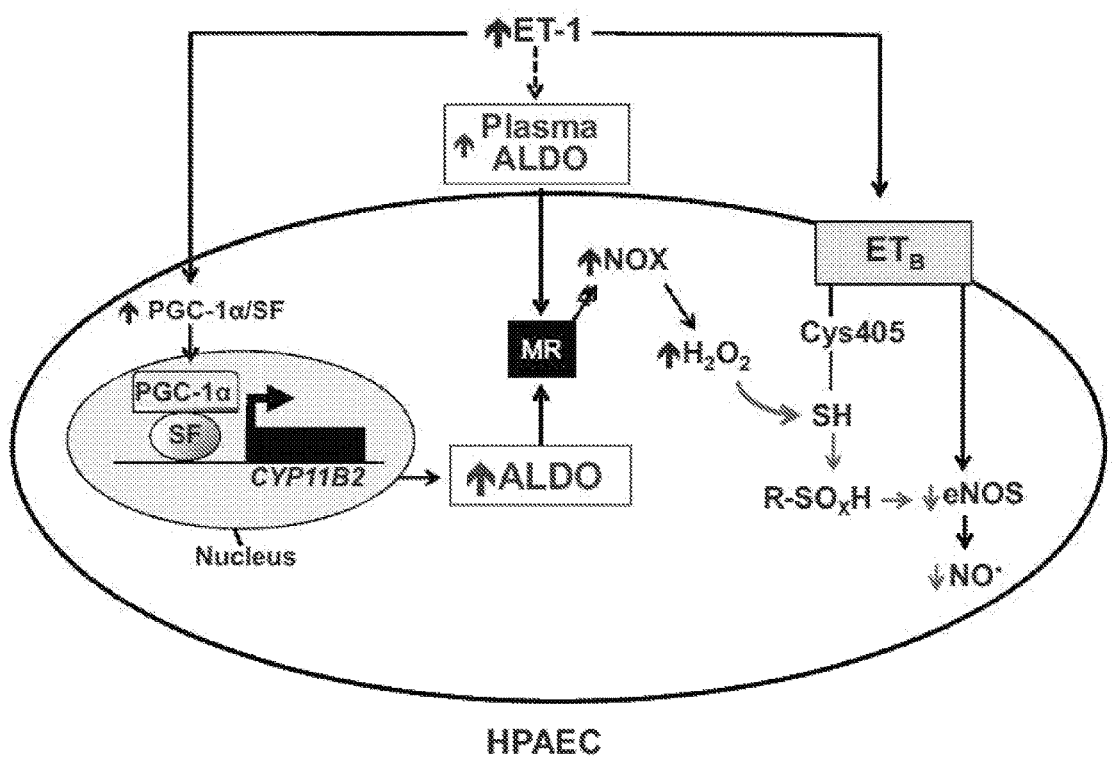
FIG. 8 depicts a schematic of a proposed mechanism by which hyperaldosteronism decreases pulmonary endothelial eNOS activation and NO. generation in PAH. Hyperaldosteronism (ALDO) in pulmonary arterial hypertension (PAH) may occur via i) endothelin-1 (ET-1)-mediated activation of PPARγ coactivator-1α (PGC-1α)/steroidogenesis factor-1 (SF) to increase CYP11B2 (aldosterone synthase) gene transcription in HPAECs, and/or ii) upregulation of adrenal ALDO synthesis via ET-1 and/or overactivation of the renin-angiotensin pathway. Stimulation of the mineralocorticoid receptor (MR) in HPAECs by ALDO activates NADPH oxidase type 4 (NOX4) to increase levels of hydrogen peroxide ($H_2O_2$), which, in turn, oxidatively modifies redox sensitive, functional cysteinyl thiol(s) in the $ET_B$ receptor (Cys405) to impair $ET_B$-dependent activation of eNOS and decrease synthesis of nitric oxide (NO.). eNOS, endothelial nitric oxide synthase; R—$SO_xH$, higher oxidative intermediaries of cysteine.

The experiments described herein demonstrate that elevated levels of ET-1 in PAH are associated with increased plasma and lung tissue levels of aldosterone, indicating that the pathophysiological effects attributed to ET-1 is, at least in part, a result of systemic and local hyperaldosteronism. This conclusion was confirmed in vivo by demonstrating that the mineralocorticoid receptor antagonists spironolactone or eplerenone, given in the absence of ET-1 blockade, decreased PASP, RV hypertrophy, PVRi, and pulmonary vascular remodeling. These effects did not occur as a result of changes in left-sided hemodynamics or differences in plasma ET-1 levels as a result of mineralocorticoid receptor blockade. It was demonstrated that ET-1 increases aldosterone levels through a mechanism that involves upregulation of CYP11B2, the rate-limiting enzyme in aldosterone synthesis, in a PGC-1α/SF-dependent manner. The functional consequences of elevated aldosterone levels include increased oxidant stress and decreased bioavailable NO. Although diminished NO. levels resulted, in part, from its consumption by ROS as demonstrated by an increase in $ONOO^-$ formation, also found was a novel mechanism to explain the aldosterone-mediated decrease in ET-1-stimulated NO. formation: oxidation of cysteinyl thiols (Cys405) in the eNOS-activating region of the $ET_B$ receptor (to sulfenic acid and the disulfide form) (FIG. 8). Thus, aldosterone contributes to high pulmonary vascular tone by oxidizing cysteinyl thiols in $ET_B$, which, in turn, acts as a redox switch to impair ET-1-stimulated endothelial NO. generation.

The data described herein indicate that aldosterone antagonism can be of benefit when started early in the disease course or when PAH is established.

The data described herein implicate ET-1 as the stimulus for increased lung tissue and plasma aldosterone levels in PAH. Using the MCT rat model of PAH, a 3-fold increase in plasma ET-1 levels was confirmed/ The levels of ET-1 that were observed were 1000-fold higher than that required to stimulate aldosterone secretion from adrenocortical cells in vitro.[6] Furthermore, the levels of plasma ET-1 measured in this study, akin to those observed in patients with PAH,[25] were sufficient to increase plasma aldosterone levels by 406%. These plasma aldosterone levels are similar to what have been observed in patients with left-sided congestive heart failure and secondary pulmonary hypertension.[26,27] Moreover, this study likely underestimated the maximal level of hyperaldosteronism achieved in PAH as plasma levels were measured antecedent to advanced stage disease, which is associated with decreased cardiac output vis-à-vis cor pulmonale that results in a decline in PASP and compensatory (over)activation of the renin-angiotensin-aldosterone system.[27]

The mechanism by which ET-1 stimulates aldosterone secretion in HPAECs involved upregulation of the expression of CYP11B2, the rate-limiting enzyme in aldosterone biosynthesis. CYP11B2 expression in human pulmonary vascular endothelial and smooth muscle cells has been demonstrated and shown to be responsive to angiotensin II or potassium resulting in an increase in local aldosterone production.[28] In contrast, other studies performed in HPAECs failed to show an effect of angiotensin II on CYP11B2 transcription or aldosterone production;[29] however, these studies were performed on cells at passage 14 or older, which may adversely affect global vascular endothelial mRNA and protein expression levels. Moreover, this earlier study measured aldosterone production using an assay with a lower limit of detection reported to be 20 pg/ml. This study utilized a more sensitive assay with a lower limit of detection of 7 pg/ml. The observation that CYP11B2 expression was increased via upregulation of PGC-1α and its association with SF at the promoter region of the CYP11B2 gene confirms prior work in adrenal-cortex-derived Y1 cells that demonstrated a similar mechanism of CYP11B2 upregulation.[15] Also described herein is additional evidence for this mechanism by PGC-1α agonism with the thiazolidinedione, pioglitazone.

The adverse effects of aldosterone on the systemic vasculature include increased oxidant stress and decreased bioavailable NO. that promotes endothelial dysfunction and impairs vascular reactivity.[4, 7, 26, 33] The finding described herein of increased pulmonary endothelial oxidant stress is not surprising as others have reported an increase in reactive oxygen species production owing to increased NOX1 expression in the small muscularized arteries isolated from the MCT-rat model of PAH.[34] Here, the experiments focused selectively on oxidant stress in the endothelium and found an increase in expression of NOX4 and the NOX4 subunit p22$^{phox}$, indicating that both NOX1 and NOX4 systems may be operative in PAH. Furthermore, the in vitro studies described herein attribute this increase in NADPH oxidase activity to aldosterone and not to ET-1. Conversely, other studies have reported that ET-1 decreased $H_2O_2$ production in fetal pulmonary artery endothelial cells in an $ET_B$-dependent manner;[35] however, these studies were not performed in a timeframe that would afford upregulation of aldosterone synthesis by ET-1.

In the setting of increased oxidant stress, NO. reacts with superoxide to form ONOO$^-$, which was observed in the experiments described herein. Other previously suggested mechanisms include uncoupling of eNOS to form superoxide in preference to NO., upregulation of arginase II,[36] oxidation of tetrahydrobiopterin,[37] altered S-nitrosoglutathione reductase activity,[38] and caveolin-1 deficiency.[39] Identified herein is a new additional mechanism to explain the decrease in eNOS activity and bioavailable NO.: dysfunctional ET-1/$ET_B$-eNOS signaling in the setting of elevated aldosterone levels owing to oxidative posttranslational modification of redox-sensitive cysteinyl thiol(s) in the $ET_B$ receptor. Oxidation of cysteine residues to form higher oxidative intermediates of cysteine, including the disulfide form, is known to occur under conditions of oxidant stress and to regulate protein function.[40]

The $ET_B$ receptor is a 7 transmembrane domain G-coupled protein receptor with a carboxy-terminal cystoplasmic tail that contains 3 functional cysteine residues: Cys402, Cys403, and Cys405.[9] As described herein, these cysteines are oxidatively modified, which is associated with functional consequences for $ET_B$-dependent eNOS activity. Without wishing to be bound by theory, it appears that these cysteines, e.g. Cys405, function as a redox switch to modulate eNOS activity. In support of this concept is the observation made herein that site-directed mutagenesis of Cys405 rendered $ET_B$ resistant to oxidant stress-induced sulfenic acid and disulfide formation, and, as a result, improved redox-sensitive signaling.

In summary, described herein is aldosterone as an unrecognized biological intermediate that modulates the adverse vascular effects of ET-1 in PAH. Further described is a novel mechanism by which to explain the defect in ET-1/$ET_B$-eNOS signaling associated with PAH: oxidative posttranslational modification of the $ET_B$ receptor. The observations made herein demonstrate further that a class effect exists for mineralocorticoid receptor antagonists and that these agents ameliorate the PAH phenotype by improving pulmonary hemodynamics and (mal)adaptive pulmonary vascular remodeling. Collectively, these findings indicate that mineralocorticoid receptor antagonism in PAH may represent a novel pharmacotherapeutic strategy to improve pulmonary vascular dysfunction and its attendant sequelae in patients with PAH.

References
1. Archer S L, Weir E K, Wilkins M R. Basic science of pulmonary arterial hypertension for clinicians: new concepts and experimental therapies. *Circulation*. 2010;121(18):2045-2066.
2. Farber H W, Loscalzo J. Pulmonary arterial hypertension. *N Engl J Med*. 2004;351(16):1655-1665.
3. Michelakis E D. The role of the NO axis and its therapeutic implications in pulmonary arterial hypertension. *Heart Fail Rev*. 2003;8(1):5-21.
4. Leopold J A, Dam A, Maron B A, Scribner A W, Liao R, Handy D E, Stanton R C, Pitt B, Loscalzo J. Aldosterone impairs vascular reactivity by decreasing glucose-6-phosphate dehydrogenase activity. *Nat Med*. 2007;13(2):189-197.
5. Weber K T. Aldosterone in congestive heart failure. *N Engl J Med*. 2001;345(23):1689-1697.
6. Rossi G P, Albertin G, Neri G, Andreis P G, Hofmann S, Pessina A C, Nussdorfer G G. Endothelin-1 stimulates steroid secretion of human adrenocortical cells ex vivo via both ETA and ETB receptor subtypes. *J Clin Endocrinol Metab*. 1997;82(10):3445-3449.
7. Maron B A, Zhang Y Y, Handy D E, Beuve A, Tang S S, Loscalzo J, Leopold J A. Aldosterone increases oxidant stress to impair guanylyl cyclase activity by cysteinyl thiol oxidation in vascular smooth muscle cells. *J Biol Chem*. 2009;284(12):7665-7672.
8. Hirata Y, Emori T, Eguchi S, Kanno K, Imai T, Ohta K, Marumo F. Endothelin receptor subtype B mediates synthesis of nitric oxide by cultured bovine endothelial cells. *J Clin Invest*. 1993;91(4):1367-1373.
9. Okamoto Y, Ninomiya H, Tanioka M, Sakamoto A, Miwa S, Masaki T. Palmitoylation of human endothelinB. Its critical role in G protein coupling and a differential requirement for the cytoplasmic tail by G protein subtypes. *J Biol Chem*. 1997;272(34):21589-21596.
10. Oka M, Homma N, Taraseviciene-Stewart L, Morris K G, Kraskauskas D, Burns N, Voelkel N F, McMurty I F. Rho kinase-mediated vasoconstriction is important in severe occlusive pulmonary arterial hypertension in rats. *Circ Res*. 2007;100(6):923-929.
11. Guo C, Ricchiuti V, Lian B Q, Yao T M, Coutinho P, Romero J L, Li J, Williams G H, Adler G K. Mineralocorticoid receptor blockade reverses obesity-related changes in expression of adiponectin, peroxisome proliferator-activated receptor-gamma, and proinflammatory adipokines *Circulation*. 2008;117(17):2253-2261.
12. Zhang T T, Cui B, Dai D Z, Su W. CPU 86017, p-chlorobenzyltetrahydroberberine chloride, attenuates monocrotaline-induced pulmonary hypertension by suppressing endothelin pathway. *Acta Pharmacol Sin*. 2005;26(11):1309-1316.
13. Jones J E, Walker J L, Song Y, Weiss N, Cardoso W V, Tuder R M, Loscalzo J, Zhang Y Y. Effect of 5-lipoxygenase on the development of pulmonary hypertension in rats. *Am J Physiol Heart Circ Physiol*. 2004;286(5):H1775-1784.
14. Morishita R, Higaki J, Ogihara T. Endothelin stimulates aldosterone biosynthesis by dispersed rabbit adreno-capsular cells. *Biochem Biophys Res Commun*. 1989;160(2):628-632.
15. Zhu L, Ke Y, Shao D, Cui Y, Qiao A, Liu X, Fang F, Chang Y. PPARgamma co-activator-1 alpha co-activates steroidogenic factor 1 to stimulate the synthesis of luteinizing hormone and aldosterone. *Biochem J*. 2010;432(3):473-483.

16. Hashikabe Y, Suzuki K, Jojima T, Uchida K, Hattori Y. Aldosterone impairs vascular endothelial cell function. *J Cardiovasc Pharmacol.* 2006;47(4):609-613.
17. Touyz R M, Briones A M, Sedeek M, Burger D, Montezano A C. NOX isoforms and reactive oxygen species in vascular health. *Mol Interv.* 2011;11(1):27-35.
18. Kedzierski R M, Yanagisawa M. Endothelin system: the double-edged sword in health and disease. *Annu Rev Pharmacol Toxicol.* 2001;41:851-876.
19. Gunaydin H, Houk K N. Mechanisms of peroxynitrite-mediated nitration of tyrosine. *Chem Res Toxicol.* 2009; 22(5):894-898.
20. Maller C, Schröder E, Eaton P. Glyceraldehyde 3-phosphate dehydrogenase is unlikely to mediate hydrogen peroxide signaling: studies with a novel anti-dimedone sulfenic acid antibody. *Antioxid Redox Signal* 2011;14(1): 49-60.
21. Hu Z, Chen J, Wei Q, Xia Y. Bidirectional actions of hydrogen peroxide on endothelial nitric-oxide synthase phosphorylation and function: co-commitment and interplay of Akt and AMPK. *J Biol Chem.* 2008;283(37): 25256-25263.
22. Martyniuk T V, Chazova I E, Masenko V P, Volkov V N, Belenkov Iu N. [Activity of renin-angiotensin-aldosterone system (RAAS) and vasopressin level in patients with primary pulmonary hypertension]. *Ter Arkh.* 1998;70(4): 33-36.
23. Kokubu T, Kazatani Y, Hamada M, Matsuzaki K, Ito T, Nishimura K, Ochi T, Daimon F, Joh T. Is captopril effective in primary pulmonary hypertension? *Jpn Circ J.* 1982;46(10):1095-1097.
24. Bansal S, Badesch D, Bull T, Schrier R W. Role of vasopressin and aldosterone in pulmonary arterial hypertension: A pilot study. *Contemp Clin Trials.* 2009;30(5): 392-399.
25. Cacoub P, Dorent R, Nataf P, Carayon A. Endothelin-1 in pulmonary hypertension. *N Engl J Med.* 1993;329(26): 1967-1968.
26. Rousseau M F, Gurne O, Duprez D, Van Mieghem W, Robert A, Ahn S, Galanti L, Ketelslegers J M. Beneficial neurohormonal profile of spironolactone in severe congestive heart failure: results from the RALES neurohormonal substudy. *J Am Coll Cardiol.* 2002;40(9):1596-1601.
27. Usui S, Yao A, Hatano M, Kohmoto O, Takahashi T, Nagai R, Kinugawa K. Upregulated neurohumoral factors are associated with left ventricular remodeling and poor prognosis in rats with monocrotaline-induced pulmonary arterial hypertension. *Circ J.* 2006;70(9):1208-1215.
28. Takeda Y, Miyamori I, Yoneda T, Hatakeyama H, Inaba S, Furukawa K, Mabuchi H, Takeda R. Regulation of aldosterone synthase in human vascular endothelial cells by angiotensin II and adrenocorticotropin. *J Clin Endocrinol Metab.* 1996;81(8):2797-2800.
29. Ahmad N, Romero D G, Gomez-Sanchez E P, Gomez-Sanchez C E. Do human vascular endothelial cells produce aldosterone? *Endocrinology.* 2004;145(8):3626-3629.
30. Zanchi A, Chiolero A, Maillard M, Nussberger J, Brunner H R, Burnier M. Effects of the peroxisomal proliferator-activated receptor-gamma agonist pioglitazone on renal and hormonal responses to salt in healthy men. *J Clin Endocrinol Metab.* 2004;89(3):1140-1145.
31. Zhang H, Zhang A, Kohan D E, Nelson R D, Gonzalez F J, Yang T. Collecting duct-specific deletion of peroxisome proliferator-activated receptor gamma blocks thiazolidinedione-induced fluid retention. *Proc Natl Acad Sci USA.* 2005;102(26):9406-9411.
32. Uruno A, Matsuda K, Noguchi N, Yoshikawa T, Kudo M, Satoh F, Rainey W E, Hui X G, Akahira J, Nakamura Y, Sasano H, Okamoto H, Ito S, Sugawara A. Peroxisome proliferator-activated receptor-{gamma} suppresses CYP11B2 expression and aldosterone production. *J Mol Endocrinol.* 2011;46(1):37-49.
33. Farquharson C A, Struthers A D. Aldosterone induces acute endothelial dysfunction in vivo in humans: evidence for an aldosterone-induced vasculopathy. *Clin Sci (Loud).* 2002;103(4):425-431.
34. Csiszar A, Labinskyy N, Olson S, Pinto J T, Gupte S, Wu J M, Hu F, Ballabh P, Podlutsky A, Losonczy G, de Cabo R, Mathew R, Wolin M S, Ungvari Z. Resveratrol prevents monocrotaline-induced pulmonary hypertension in rats. *Hypertension.* 2009;54(3):668-675.
35. Wedgwood S, Black S M. Endothelin-1 decreases endothelial NOS expression and activity through ETA receptor-mediated generation of hydrogen peroxide. *Am J Physiol Lung Cell Mol Physiol.* 2005;288(3):L480-487.
36. Watts J A, Marchick M R, Gellar M A, Kline J A. Up-regulation of arginase II contributes to pulmonary vascular endothelial cell dysfunction during experimental pulmonary embolism. *Pulm Pharmacol Ther.* 2011;24(4): 407-413.
37. Grobe A C, Wells S M, Benavidez E, Oishi P, Azakie A, Fineman J R, Black S M. Increased oxidative stress in lambs with increased pulmonary blood flow and pulmonary hypertension: role of NADPH oxidase and endothelial NO synthase. *Am J Physiol Lung Cell Mol Physiol.* 2006;290(6):L1069-1077.
38. Brown-Steinke K, deRonde K, Yemen S, Palmer L A. Gender differences in S-nitrosoglutathione reductase activity in the lung. *PLoS One.* 2010;5(11):e14007.
39. Zhao Y Y, Zhao Y D, Mirza M K, Huang J H, Potula H H, Vogel S M, Brovkovych V, Yuan J X, Wharton J, Malik A B. Persistent eNOS activation secondary to caveolin-1 deficiency induces pulmonary hypertension in mice and humans through PKG nitration. *J Clin Invest.* 2009;119(7):2009-2018.
40. Wouters M A, Fan S W, Haworth N L. Disulfides as redox switches: from molecular mechanisms to functional significance. *Antioxid Redox Signal.* 2010;12(1):53-91.
41. Elshourbagy N A, Adamou J E, Gagnon A W, Wu H L, Pullen M, Nambi P. Molecular characterization of a novel human endothelin receptor splice variant. *J Biol Chem.* 1996;271(41):25300-25307.
42. Marrero M B, Venema V J, Ju H, He H, Liang H, Caldwell R B, Venema R C. Endothelial nitric oxide synthase interactions with G-protein-coupled receptors. *Biochem J.* 1999;343 Pt 2:335-340.
43. Mathew R, Yuan N, Rosenfeld L, Gewitz M H, Kumar A. Effects of monocrotaline on endothelial nitric oxide synthase expression and sulfhydryl levels in rat lungs. *Heart Dis.* 2002;4(3):152-158.

Example 2

Supplemental Materials & Methods

Amplex Red Activity Assay. Hydrogen peroxide levels were measured in cell lysates using the horseradish peroxidase-linked Amplex Red assay (Invitrogen) as described previously.[1]

Aldosterone and ET-1 levels. Cells were treated with ET-1 (1-100 nM), pioglitazone (50 µM/l), or angiotensin II (10

μM/l) for 24 h (all from Sigma-Aldrich). In selected experiments, cells were pre-treated for 6 h with BQ-788 (1.5 μM) (Sigma-Aldrich) to inhibit the $ET_B$ receptor. Aldosterone levels were measured in the medium of cells grown in phenol-free EGM-2 medium supplemented with charcoal-stripped serum, by enzyme immunoassay according to the manufacturer's instructions (Cayman). Results were standardized to cell protein concentration. Levels of aldosterone and ET-1 from plasma and whole lung tissue were measured by enzyme immunoassay according to the manufacturer's instructions (Cayman).

NO. metabolites. Nitrite ($NO_2^-$) and nitrate ($NO_3^-$) were measured in cell culture medium containing 2% fetal bovine serum and L-arginine (1 mmol/l) (Sigma-Aldrich) by 1(H)-naphthotriazole fluorescence (Cayman) as previously reported.[1] To measure $NO_2^-$ levels in whole lung tissue, lung specimens were harvested from rats and snap frozen in liquid nitrogen. Samples were thawed, homogenized in PBS (pH 7.4), and centrifuged at 14,000×g at 4° C. for 20 min. The supernatant was ultrafiltered using a 30 kDa molecular weight filter (Millpore), and the eluant was used to measure $NO_2^-$ levels according to manufacturer's instructions (Cayman).

Immunoblotting. Proteins were size fractionated electrophoretically using SDS-PAGE and transferred to polyvinylidene fluoride membranes. The membranes were incubated with anti-$ET_A$ (Santa Cruz Biotechnology), anti-$ET_B$ (Santa Cruz Biotechnology), anti-NOX4 (Santa Cruz Biotechnology), anti-p22$P^{phox}$ (Santa Cruz), anti-eNOS (Cell Signaling), anti-PGC-1α (Santa Cruz Biotechnology), and anti-SF (Santa Cruz Biotechnology) antibodies overnight at 4° C. and visualized using the ECL detection system (Amersham Biosciences). In experiments to assess $ET_A$ expression, purified $ET_A$ protein (Novus Biological) was loaded to serve as an internal control.

Co-immunoprecipitation of proteins. Cell monolayers were washed twice with ice-cold PBS and incubated on ice with RIPA buffer supplemented with various protease inhibitors (Millpore). Cells were scraped with a rubber policeman and samples were rotated at 4° C. for 15 min. Lysates were centrifuged at 14,000×g at 4° C. for 15 min and the then pre-cleared with a 50% slurry of Protein G agarose beads (Santa Cruz Biotechnology) mixed with PBS. Following removal of the beads by centrifugation, cell lysates were incubated with an anti-$ET_B$ or anti-PGC-1α antibody (Santa Cruz Biotechnology) overnight at 4° C. The immunocomplex was captured by incubating lysates with 50% Protein G agarose bead slurry at 4° C. for 1 h. Beads were collected by pulse centrifugation, resuspended in non-reducing sample buffer, and then boiled for 10 min to dissociate the immunocomplex from the beads. Western analysis was performed with an anti-SF (Santa Cruz) or anti-sulfenic acid (R—SOH) antibody (Millpore) as described above.

Chromatin immunoprecipitation assay. Chromatin immunoprecipitation assays were performed using the QuikChIP assay (Imgenex) according to the manufacturer's instructions. PCR amplification was performed on the proximal region of the CYP11B2 promoter region containing the gonadotrope-specific element [51]. The primers used were: forward 5'-GAGAAAGGAGAGGCCAGGTC-3' (SEQ ID NO:2) and reverse 5'-CAGGAACCTGCTCTGGAAAC-3' (SEQ ID NO: 3). CYP11B2 primers used for PCR were forward: 5' GAGAAAGGAGAGGCCAGGTC-3' (SEQ ID NO: 4) and reverse: 5'-CAGGAACCTGCTCTGGAAAC-3' (SEQ ID NO:5).

eNOS activity. eNOS activity was measured using the NOS activity kit (Cayman) according to the manufacturer's instructions with some modifications. Cells were washed with PBS containing 1 mM EDTA, transferred to a microcentrifuge tube, and centrifuged at 14,000×g at 4° C. for 2 min. The supernatant was decanted and homogenization buffer (250 mM Tris-HCl, pH 7.4, 6 μM $BH_4$, 2 μM flavin adenine dinucleotide, and 2 μM flavin adenine mononucleotide) was added to the cell pellets. The cells were lysed and exposed to [$^{14}$C] arginine (100 μCi/ml) for 2 min prior to incubation with ET-1 (10 nM) or PBS as vehicle control for 30 min at room 25° C. The samples were then centrifuged at 14,000×g for 30 seconds and radioactivity of the eluant was quantified in a liquid scintillation counter (Beckman-Coulter).

3-Nitrotyrosine immunohistochemistry. Cells grown to confluence on glass chamber slides were fixed following treatments and anti-3-nitrotyrosine immunohistochemistry (Santa Cruz Biotechnology) was performed using the 3,3'-diaminobenzidine substrate method (Vector laboratories) as described previously.[1]

Site-directed mutagenesis and transfection. cDNAs encoding wild type (WT) eNOS and WT-$ET_B$ from human were cloned into the mammalian expression vector pCMV6 (Origene). The C405A-$ET_B$ mutant was purchased from Genewiz (South Plainfield, N.J.). COS-7 cells, which do not express endogenous eNOS or $ET_B$, were plated in P100 tissue culture dishes and transfected with 10 μg of WT-eNOS and WT-$ET_B$ or C405A-$ET_B$ DNA for 4.5 h with Lipofectamine 2000™ in OptiMEM medium (Invitrogen). After this time, the medium was replaced with Dulbecco's Modified Eagle Medium (Gibco) supplemented with 10% FBS, and experiments were performed after 24 h.

Lung tissue histology. Rat lung vessels were perfused with saline through the pulmonary artery and inflated with 10% phosphate-buffered formalin at a pressure of 20 cm $H_2O$ through the trachea as described previously.[2] After fixation for 24 h at 4° C., the lung tissue was processed and embedded in paraffin using a Hypercenter™ XP System and Embedding Center (Shandon, Pittsburg, Pa.). The paraffin-embedded lung tissue was cut into 5-μm sections. Hematoxylin and eosin staining was performed according to methods published previously.[3] The 3,3'-diaminobenzidine substrate method was used for smooth muscle α-actin immunohistochemical staining. The number of muscularized arteries with a diameter of 20-50 μm located distal to terminal bronchioles were counted in 20 consecutive fields (100×) per section,[2] and the cross-sectional area was assessed using Image J™ software (NIH).

Sections were stained with a Gomori's Trichrome Staining Kit according to the manufacturer's instruction (Fischer Scientific). Image J™ software (NIH) was used to measure the per cent perivascular collagen deposition of muscularized arterioles with a diameter of 20-50 μm by subtracting the area of the lesser curvature from the greater curvature and dividing by the lesser curvature×100. Collagen was also assessed in tissue sections using Picrosirius Red Stain Kit according to the manufacturer's instruction (Polysciences). Lung sections were visualized under polarized light using an Olympus BX51™ microscope and images were acquired by the Picture Taker™ software package.

Echocardiography. Transthoracic two-dimensional, M-mode, and Doppler imaging were performed in rats using a Vevo 2010 ultrasonographic system with a 15-MHz transducer. M-mode and Doppler tracings were acquired at a sweep speed of 200 mm/s following optimization of endocardial visualization and spectral display of Doppler profiles as described previously.[3] M-mode measurements of the right ventricular free-wall thickness were measured in the parasternal short-axis view just below the levels of the aortic valve, as described previously and in accordance with recommendations on M-mode measurement of the RV by the American Society of Echocardiography.[4] All studies were performed by a cardiologist and experienced sonographer who was blinded to the treatment group and was responsible for image analysis.

Right heart catheterization. An incision was made in the anterior triangle of the right neck, and a dissection was performed to expose the right internal jugular vein. A 0.04×0.023 in.-sized polyvinylchloridine catheter with a curved end was flushed with heparinized saline and connected to a Grass pressure transducer and Grass model 79 polygraph. A 4.0-proline suture was used to achieve hemostasis at the distal end of the jugular vein prior to insertion of the catheter. The tube was advanced and RV systolic pressure was recorded, which was assumed to be equal to PASP in the setting of a normal pulmonic valve.[3] All right heart catheterizations were performed within 10 min of echocardiography and both procedures were completed within 30 min.

Left heart catheterization and hemodynamics. Following completion of the right heart catheterization, a deep neck dissection was performed to identify the right carotid artery. Without disrupting the carotid sinus or vagus nerve, a cross-clamp was applied to the proximal and distal aspects of the carotid artery. A high fidelity Millar catheter (Millar Instruments, Inc.) was inserted into the carotid artery, the distal clamp was released, and the catheter was advanced past the aortic arch to record central aortic blood pressure. The catheter was then advanced across the aortic valve and left ventricular end-diastolic pressure (LVEDP) were recorded. Cardiac index (CI) was derived from pressure-volume loop analysis as described previously.[5] The pulmonary vascular resistance index was calculated as [(mean pulmonary artery pressure-LVEDP)/CI)] and systemic vascular resistance index was calculated as [(mean arterial pressure-mean right atrial pressure)/CI].

Right ventricular weight. After sacrifice, the heart was dissected immediately. A 2-cm incision was made in the anterior aspect of the RV and LV and the residual intracavitary blood volume was exsanguinated prior to weighing the RV. Data are expressed as the ratio of RV weight (mg)/LV+septum weight (g).

References

1. Maron B A, Zhang Y Y, Handy D E, Beuve A, Tang S S, Loscalzo J, Leopold J A. Aldosterone increases oxidant stress to impair guanylyl cyclase activity by cysteinyl thiol oxidation in vascular smooth muscle cells. *J Biol Chem.* 2009;284(12):7665-7672.
2. Jones J E, Walker J L, Song Y, Weiss N, Cardoso W V, Tuder R M, Loscalzo J, Zhang Y Y. Effect of 5-lipoxygenase on the development of pulmonary hypertension in rats. *Am J Physiol Heart Circ Physiol.* 2004;286(5):H1775-1784.
3. Jones J E, Mendes L, Rudd M A, Russo G, Loscalzo J, Zhang Y Y. Serial noninvasive assessment of progressive pulmonary hypertension in a rat model. Am J Physiol Heart Circ Physiol 2002;283:H364-371.
4. Rudski L G, Lai W W, Afilalo J, Hua L, Handschumacher M D, Chandrasekaran K, Solomon S D, Louie E K, Schiller N B. Guidelines for the echocardiographic assessment of the right heart in adults: a report from the American Society of Echocardiography endorsed by the European Association of Echocardiography, a registered branch of the European Society of Cardiology, and the Canadian Society of Echocardiography. *J Am Soc Echocardiogr.* 2010;23(7):685-713; quiz 786-688.
5. Pacher P, Nagayama T, Mukhopadhyay P, Bátkai S, Kass D A. Measurement of cardiac function using pressure-volume conductance catheter technique in mice and rats. *Nat Protcol.* 2008;3(9):1422-1434.

What is claimed herein is:

1. A method of treating hypertension in a subject in need thereof, the method comprising administering to the subject an ET-B polypeptide comprising an oxidant-resistant mutation at Cys405, Cys403, or Cys402.

2. The method of claim 1, wherein the subject is in need of treatment for a condition selected from the group consisting of:
systemic hypertension and pulmonary arterial hypertension.

3. The method of claim 1, wherein the oxidant-resistant mutation is the substitution of a cysteine with an alanine, valine, leucine, or isoleucine.

4. The method of claim 1, wherein the oxidant-resistant mutation at Cys405 is selected from: Cys405Ala; Cys405Val; Cys405Leu; and Cys405Ile.

5. A method of treating hypertension in a subject in need thereof, the method comprising administering to the subject a nucleic acid encoding an ET-B polypeptide comprising an oxidant-resistant mutation at Cys405, Cys403, or Cys402.

6. The method of claim 5, wherein the oxidant-resistant mutation is the substitution of a cysteine with an alanine, valine, leucine, or isoleucine.

7. The method of claim 5, wherein the oxidant-resistant mutation at Cys405 is selected from: Cys405Ala; Cys405Val; Cys405Leu; and Cys405Ile.

8. The method of claim 5, wherein the subject is in need of treatment for a condition selected from the group consisting of:
systemic hypertension and pulmonary arterial hypertension.

* * * * *